(12) United States Patent
Bocola et al.

(10) Patent No.: US 9,926,536 B2
(45) Date of Patent: Mar. 27, 2018

(54) GLUCOSE OXIDASE VARIANTS AND METHODS OF USING THE SAME

(71) Applicant: Roche Diabetes Care, Inc., Indianapolis, IN (US)

(72) Inventors: Marco Bocola, Aachen (DE); Hartmut Duefel, Schlehdorf (DE); Erik Uwe Arango Gutierrez, Aachen (DE); Dieter Heindl, Munich (DE); Thomas Meier, Munich (DE); Hemanshu Mundhada, Lyngby (DK); Ulrich Schwaneberg, Kelmis-Hergenrath (BE); Michael Tacke, Munich (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 14/810,070

(22) Filed: Jul. 27, 2015

(65) Prior Publication Data
US 2016/0002609 A1    Jan. 7, 2016

Related U.S. Application Data

(63) Continuation of application No. PCT/EP2014/051602, filed on Jan. 28, 2014.

(30) Foreign Application Priority Data

Jan. 28, 2013  (EP) .................................... 13152935

(51) Int. Cl.
| C12N 9/20 | (2006.01) |
| C12N 9/04 | (2006.01) |
| C12N 9/54 | (2006.01) |
| C12Q 1/54 | (2006.01) |

(52) U.S. Cl.
CPC ............. *C12N 9/0006* (2013.01); *C12N 9/54* (2013.01); *C12Q 1/54* (2013.01); *C12Y 101/03004* (2013.01); *G01N 2333/904* (2013.01)

(58) Field of Classification Search
None
See application file for complete search history.

(56) References Cited

U.S. PATENT DOCUMENTS

| 5,516,671 A * | 5/1996 | Lawrence | A01N 63/00 435/69.1 |
| 6,376,210 B1 * | 4/2002 | Yuan | C12Q 1/25 435/18 |
| 8,999,140 B2 * | 4/2015 | Kojima | C12Q 1/006 204/403.01 |

FOREIGN PATENT DOCUMENTS

| EP | 354441 A2 | 2/1990 |
| EP | 2415863 A1 | 8/2012 |

OTHER PUBLICATIONS

Altschul, Stephen et al., Basic Local Alignment Search Tool, J. Mol. Biol., 1990, 403-410, 215.
Altschul, Stephen et al., Gapped Blast and PSI-Blast: a new generation of, Nucleic Acids Research, 1997, 3389-3402, 25, No. 17, Oxford University Press.
Bankar, Sandip et al., Glucose oxidase An overview, Biotechnology Advances, 2009, pp. 489-501, 27.
Bentlex, R. et al., The Mechanism of the Action of Notatin, Biochem. J., 1949, 584-590, 45.
Berchmanns, Sheela et al., Layer-by-layer assembly of 1,4-diaminoanthraquinone, Materials Chemistry and Physics, 2002, pp. 390-396, 77, Central Electrochemical Research Institute, Karaikudi.
Bhatti, H.N. et al., Purification and thermodynamic characterization of glucose oxidase from a newly isolated strain of Aspergillus niger, Canadian Journal of Microbiology, 2006, 519-524, vol. 52.
Dennig, Alexander et al., OmniChange: The Sequence Independent Method for, Plos One, 2011, Issue 10, e26222, 6.
Frederick, Katherine R. et al., Glucose Oxidase from Aspergillus niger, The Journal of Biological Chemistry, 1990, 3793-3802, vol. 265, Issue of Mar. 5, 1990.
Gietz, Daniel et al., High-efficiency yeast transformation using the, Nature Protocols, 2007, pp. 31-34, 2, No. 1, Nature Publishing Group.
Hayashi, Sueko et al., Multiple Forms of Glucose Oxidase With Different Carbohydrate Compositions, Biochimica et Biophysica Acta, 1981, pp. 40-51, 657, Elsevier/North-Holland Biomedical Press.
Hecht, H.J. et al., Crystal Structure of Glucose Oxidase from Aspergillus niger Refined at 2.3 Angstrom Resolution, J. Mol. Biol., 1993, pp. 153-172, 229, Academic Press Limited.
Hecht, H.J. et al., The 3D structure of glucose oxidase from Apergillus niger. Implications for the use of GOD as a biosensor enzyme, Biosensors & Bioelectronics, 1993, pp. 197-203, 8, Elsevier Science Publishers Ltd.
Hoenes, Joachim et al., The Technology Behind Glucose Meters: Test Strips, Diabetes Technology & Therapeutics, 2008, pp. S-10-S-26, vol. 10, Supplement 1.
Horaguchi, Yohei et al., Turning glucose oxidase into essentially dehydrogenase, Honolulu PRiME, 2012, 2057, MA2012-02, Issue 18, The Electrochemical Society.
Lehle, Ludwig et al., Glycoprotein biosynthesis in *Saccharomyces cerevisiae:* ngd29, an N-glycosylation mutant allelic to ochl having a defect in the initiation of outer chain formation, FEBS Letters, 1995, pp. 41-45, 370, Federation of European Biochemical Societies.
Leskovac, V. et al., Glucose oxidase from Aspergillus niger: the mechanism of action, The International Journal of Biochemistry & Cell Biology, 2005, pp. 731-750, 37, Elsevier Ltd.

(Continued)

*Primary Examiner* — Hope Robinson

(57) ABSTRACT

Novel glucose oxidase (GOx) variants are disclosed that have the substitutions of T30V and I94V set forth in SEQ ID NO:1, and additionally at least one further amino acid substitution in the enzyme sequence in any of the positions S53; A137; A173; A332; F414 and V560. The GOx variants herein exhibit specificity for glucose and significantly reduced oxygen consumption rates and/or increased enzyme activity for electron mediators other than oxygen. Also provided are assay devices incorporating at least one of the GOx variants herein for improved blood glucose measurements.

12 Claims, 11 Drawing Sheets

(56) References Cited

OTHER PUBLICATIONS

Momeu, Iuliana Carmen, Improving Glucose Oxidase Properties by Directed Evolution, Thesis, 2007, 110, Thesis.

Oldeburg, Kevin et al., Recombination-mediated PCR-directed plasmid, Nucleic Acids Research, 1997, 451-452, 25, No. 2, Oxford University Press.

Olsthoorn, Arjen et al., On the Mechanism and Specificity of Soluble, Quinoprotein Glucose, Biochemistry, 1998, 13854-13861, 37, American Chemical Society.

Pazur, John et al., A Glycoprotein Structure for Glucose Oxidase from Aspergillus niger, Archives of Biochemistry and Biophysics, 1965, 351-357, 111.

Pazur, John et al., The oxidation of glucose and related compounds by glucose oxidase from apergillus niger, Biochemistry, 1964, 578-583, 3, No. 4.

Prevoteau, Antonin et al., Deglycosylation of glucose oxidase to improve biosensors and biofuel cells, Electrochemistry Communications, 2010, 213-215, 12(2), Elsevier B.V.

Sun, Lianhong et al., Modification of Galactose Oxidase to, ChemBioChem 2002, 2002, 781-783, 8, Wiley-VCH Verlag GmbH.

WHO and IDF, Definition and diagnosis of *diabetes mellitus* and intermediate hyperglycemia, Definition and diagnosis of *diabetes mellitus* and intermediate hyperglycemia, 2006, pp. 1-50, 2006 Publication, World Health Organization 2006.

Wohlfahrt, Gerd et al., 1.8 and 1.9 A resolution structures of the Penicillium amagasakiense and Aspergillus niger glucose oxidases as a basis for modelling substrate complexes, Acta Crystallographica Section D, 1999, 969-977, D55, International Union of Crystallography.

Zhu, Ziwei et al., Directed evolution of glucose oxidase from Aspergillus niger for ferrocenemethanol-mediated electron transfer, Biotechnol. J. 2007, 2007, 241-248, 2, Wiley-VCH Verlag GmbH & Co.

Zhu, Ziwei et al., Making glucose oxidase fit for biofuel cell applications by directed protein evolution, Biosensors and Bioelectronics, 2006, 2046-2051, 21.

* cited by examiner

| Residual activity [%] | GOx-WT | GOx-T30V; I94V | GOx variant EZ07 |
|---|---|---|---|
| Glucose | 100±1.05 | 100±2.1 | 100±0.3 |
| Maltose | n.d. | n.d. | n.d. |
| Galactose | 1.08±0.08 | 1.03±0.02 | 0.42±0.02 |
| Xylose | 0.38±0.04 | 0.33±0.02 | 1.66±0.01 |
| Maltotriose | 0.17±0.01 | 0.82±0.03 | 0.26±0.01 |

Fig. 8

| | $V_{max}$ [U/mg] Mediator assay | $K_M$ [mM] Mediator assay | $V_{max}$ [U/mg] ABTS assay | $K_M$ [mM] ABTS assay |
|---|---|---|---|---|
| GOx-WT | 7.40±0.12 | 13.18±1.03 | 451.10±10.98 | 14.20±1.28 |
| GOx-T30V; I94V | 13.70±0.19 | 11.85±0.86 | 586.40±16.98 | 8.82±1.12 |
| GOx variant EZ07 | 47.47±1.00 | 28.20±1.98 | 78.86±0.58 | 1.31±0.07 |

Fig. 9

GLUCOSE OXIDASE VARIANTS AND METHODS OF USING THE SAME

CROSS-REFERENCE TO RELATED APPLICATIONS

This patent application is a continuation of Int'l Patent Application No. PCT/EP2014/051602; filed 28 Jan. 2014, which claims priority to and the benefit of EP Patent Application No. 13152935.6; filed 28 Jan. 2013. Each patent application is incorporated herein by reference as if set forth in its entirety.

REFERENCE TO SEQUENCE LISTING SUBMITTED ELECTRONICALLY

An official copy of a Sequence Listing is submitted electronically via EFS-Web as an ASCII-formatted Sequence Listing with a file named "31354SquenceListing.txt," created on 27 Jul. 2015, and having a size of 68 KB. The Sequence Listing is filed concurrently with the Specification, is a part thereof and is incorporated herein by reference as if set forth in its entirety.

TECHNICAL FIELD

This patent application relates to chemistry, medicine and molecular biology, and more particularly, relates to glucose oxidase (GOx) variants exhibiting significantly reduced oxygen consumption rates. Additionally, the GOx variants are specific for glucose, and thereby exhibit not only significantly reduced oxygen consumption rates but also increased enzymatic activity for electron mediators other than oxygen.

BACKGROUND

Diabetes mellitus reflects a metabolic disease, which can be found extensively all over the world. Persons with diabetes (PWD) have an impaired or missing production of the hormone insulin, which controls the blood-glucose level, and thus these persons bear a risk of hyperglycemia as well as hypoglycemia in case of inadequate insulin application [Definition and diagnosis of diabetes mellitus and intermediate hyperglycaemia. WHO, and IDF (2006); WHO Document Production Service ISBN 9241594934].

To ensure a correct application of insulin, highly specific, accurate and easy to handle glucose measurement systems are needed for both self-measurement systems and high-throughput measurement systems on clinical scale.

To allow the adequate determination of glucose concentrations in the blood and to make the measurement highly specific, enzymatic reactions are involved. These days, the two types of enzymes that are used in diabetes analytics are reflected by the glucose dehydrogenases (GDH(s)) and glucose oxidases (GOx(s)) [Hönes et al. (2008) Diabetes Technol. Therap. 10:10-26].

The main advantage of GDHs is their oxygen-independent oxidation of glucose, but these enzymes show slight side-activities on certain other clinical relevant sugars, and thus GDHs can be unspecific [Olsthoorn & Duine (1998) Biochem. 37:13854-13861]. By contrast, the GOxs are highly specific for glucose, but their oxidation is strongly oxygen-dependent [Bankar et al. (2009) Biotechnol. Advances 27:489-501; and Bentley & Neuberger (1949) Biochem. J 45:584-590].

In more detail, GOxs as flavoproteins belong to the family of oxidoreductases (i.e., β-D-glucose:oxygen 1-oxidoreductase). Native or wild-type (WT) GOxs catalyze an oxidation of β-D-glucose to D-glucono-δ-lactone and hydrogen peroxide ($H_2O$) by employing molecular oxygen as an electron acceptor [see e.g., Pazur & Kleppe (1964) Biochem. 3:578-583]. The reaction is depicted by the following formula:

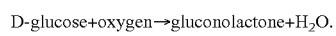

D-glucose+oxygen→gluconolactone+$H_2O$.

The substrates of the GOxs can be divided into two (2) groups: (i) the electron acceptors of the oxidative half reaction; and (ii) the electron donors of the reductive half reaction [see e.g., Leskovac et al. (2005) Int. J. Biochem. Cell Biol. 37:731-750]. One of skill in the art is aware that apart from D-glucose various derivatives of D-glucose are potential substrates for the reductive half reaction of GOxs.

GOxs from different origins have been described so far. For instance, the GOx from marine algae Chondrus crispus is described in U.S. Pat. Nos. 7,544,795 and 6,924,366; the GOx from filamentous fungi Cladosporium spec. is described in Intl Patent Application Publication Nos. WO 95/29996 and WO 1998/020136; and the GOx from Talaromyces flavus is described in U.S. Pat. No. 6,054,318.

The best-described GOx in literature is from Aspergillus niger [Hecht et al. (1993) Biosens. Bioelectron. 8:197-203; and Wohlfahrt et al. (1999) Acta Crystallographica Section D Biological Crystallography 55:969-977].

Int'l Patent Application Publication No. WO 89/126675 describes producing GOxs from A. niger in recombinant systems, and Int'l Patent Application Publication No. WO 2008/079227 describes a GOx obtained from A. niger formulated in a composition conferring improved storage stability.

GOx is a well-characterized protein forming a dimer of 160 kDa in size, and crystal structures have been solved thereof [Hecht et al. (1993) J. Mol. Biol. 229:153-172].

It is further known that particularly the wild-type GOx of A. niger (GOx-WT) exhibits significant temperature stability and specificity for the substrate glucose. Additionally, GOx is a glycoprotein with a high-mannose type carbohydrate content of 10%-16% [Hayashi & Nakamura (1981) Biochim. Biophys. Acta 657:40-51; and Pazur et al. (1965) Arch Biochem. Biophys. 111:351-357].

These days, GOxs are commonly used in test elements such as biosensors for detecting glucose either in industrial solutions or in bodily fluids of a subject (e.g., in blood and urine).

Many currently available self-measurement devices are electrochemical biosensors consisting in principle of (a) a biological component (i.e., the respective enzyme having glucose as substrate); (b) an indicator (the electronic component); and (c) a signal transducer.

In the measurement device, electrons from the glucose are transferred by the biological component (a) to an electrode via mediators (b). A signal transducer (c) then converts the electrical signal into a real-time glucose concentration, which is proportional to the amount of transferred electrons.

Apart from the above-described electrochemical sensors, photometric sensors also are available. The difference here is that the electrons from the glucose are transferred to redox-indicator dye (serving as indicator). The resulting color change of the reduced dye is measured photometrically.

Another main application might be using GOxs in the anodic compartment of implanted and miniaturized biofuel cells burning glucose from the blood stream and thereby powering miniature diagnostic devices or pumps.

Moreover, GOx applications in the food industry are numerous, since its capability of generating $H_2O_2$, which has an anti-microbial effect, and can be utilized to improve the storage stability of certain food products including cheese, butter and fruit juice.

Applications of GOxs in cosmetic compositions may utilize the anti-microbial properties as well. Potential uses for hexose oxidases in pharmaceutical and cosmetic compositions were suggested in U.S. Pat. Nos. 6,924,366 and 6,251,626, as well as Int'l Patent Application Publication No. WO 2007/045251.

Furthermore, GOx can be used to produce transgenic plants and other organisms with reduced susceptibility or increased resistance to pests or diseases (see e.g., Int'l Patent Application Publication No. WO 1995/021924).

However, use of GOxs in glucose biosensors is of significant interest in accordance with this disclosure. In this regard, Int'l Patent Application Publication No. WO 2009/104836 describes a glucose biosensor including a genetically engineered GOx variant improved for attaching to metal surfaces.

GOx mutants derived from *A. niger* are known and are mutated in T30V and/or I94V. Likewise, the corresponding double-mutant T30V; I94V is known [Zhu et al. (2006) *Biosens. Bioelectron.* 21:2046-2051; and Zhu et al. (2007) *Biotechnol. J.* 2:241-248].

Specifically, the above-mentioned T30V and I94V double-mutant exhibits slightly increased enzyme activity ($k_{cat}$ from 69.5/s to 137.7/s), exhibits an increased thermostability in a range of 58° C. to 62° C., and exhibits an improved pH stability in a range of 8 to 11 when compared to GOx-WT. However, the double-mutant derived from *A. niger* exhibits equal oxygen consumption rates when compared to the GOx-WT.

EP Patent Application Publication No. 3 415 863 describes nucleic acid molecules and polypeptides thereof having GOx activity but being mutated in at least three (3) of the following amino acid positions: 2, 13, 30, 94 and 152. Particularly, the M12 variant having the substitutions N2Y, K13E, T30V, I94V and K152R shows, besides an increased expression level in *S. cerevisiae*, a twice-increased activity for oxygen as electron acceptor.

Horaguchi et al. identified one amino acid residue position being involved in the oxidative half reaction of the GOx variants described therein, being it the GOx of *Penicillium amagasakiense* and the GOx variant of *A. niger* [Horaguchi et al. (2012) *Meet. Abstr.* MA2012-02 18:2057]. The one position is S114 of the *P. amagasakiense* GOx variant, and the corresponding T110 of the *A. niger* variant. Both positions were replaced by the amino acid Ala leading to a decrease in activity for oxygen as electron acceptor. For instance, the GOx variant of *A. niger* exhibited a 6.6-fold reduced oxygen consumption, and thus had a residual oxygen activity of 30.4% besides a mediator activity of 363%.

One drawback of GDHs is that they generally are unspecific for glucose, and the oxygen-dependent GOxs represent the key enzymes of current glucose measurement systems.

The solution to the underlying problem is providing specifically modified and thus optimized GOx variants derived from *A. niger*.

Surprisingly and unexpectedly, this disclosure provides novel GOx variants derived from *A. niger* that are specific for glucose, but independent from oxygen for glucose oxidation and thus more accurate for glucose measurements. Moreover, this disclosure provides novel GOx variants that are specific for glucose, and thereby exhibit significantly reduced oxygen consumption rates and/or significantly increased mediator activity for electron mediators other than oxygen.

The GOx variants herein, having besides the two substitutions T30V and I94V according to SEQ ID NO:1, additionally at least one amino acid substitution in any of the six (6) positions selected from: S53; A137; A173; A332; F414 and V560.

The optimized GOx variants herein are suitable to be implemented in improved blood-glucose measurement systems.

BRIEF SUMMARY

An inventive concept encompassed herein is GOx variants having double-mutant T30V; I94V (GOx-T30V; I94V) as a basis for further specific amino acid substitution(s) to obtain oxygen-independent GOx variants having a significantly reduced oxidase activity and concomitantly a significantly increased dehydrogenase activity while remaining specific for the substrate glucose. Moreover, the GOx variants herein exhibit, additionally or alone, a significantly increased mediator activity for electron mediators other than oxygen. In this regard, the GOx variants herein accept certain electron mediators other than oxygen for electron transfer. Thus, the GOx variants herein are suitable for improved glucose measurements, in particular for improved blood-glucose measurements.

The GOx variants herein can be derived from *A. niger* having, besides the two substitutions T30V and I94V according to SEQ ID NO:1, additionally at least one amino acid substitution in any of the six (6) positions selected from: S53; A137; A173; A332; F414 and V560.

In some instances, the GOx variants herein can be derived from *A. niger* having, besides the two substitutions T30V and I94V according to SEQ ID NO:1, additionally at least one amino acid substitution in any of the four (4) positions selected: A173; A332; F414 and V560.

In some instances, the GOx variants herein can have at least two, three, four, or five, or even six cooperative, and thus diverse amino acid substitutions in any of the six (6) positions selected from: S53; A137; A173; A332; F414 and V560 of the GOx according to SEQ ID NO:1, leading to a significant decrease in oxygen consumption rates.

In some instances, the GOx variants herein can have at least two, three, four, five, or even six cooperative, and thus diverse amino acid substitutions in any of the six (6) positions selected from: S53; A137; A173; A332; F414 and V560 of the GOx according to SEQ ID NO:1, leading to a significant decrease in oxygen consumption rates and/or a significant increase in mediator-activity for certain electron-mediators other than oxygen.

Advantageously, GOx variants herein possess significantly reduced oxidase activity when compared to GOx-WT and GOx-T30V; I94V according to SEQ ID NO:1, while at the same time the variants' dehydrogenase activity is significantly increased when compared to GOx-WT (SEQ ID NO:2) and GOx-T30V; I94V (SEQ ID NO:1).

Advantageously, GOx variants herein having specific amino acid substitutions in the positions F414 and V560 possess significantly reduced oxygen consumption rates when compared to GOx-WT and GOx-T30V; I94V in an ABTS assay as outlined in the Materials and Methods section under item gg). Suitable amino acids for the substitutions are all remaining nineteen (19) proteinogenic amino acids. In particular, suitable amino acids are Arg, Asn, Asp, Cys, Gly, His, Met, Ile, Leu, Ser, Thr, Tyr and Val for position F414, and Ala, Ile, Leu, Met, Pro, Tyr, Thr and Val for position V560.

Advantageously, GOx variants herein having specific amino acid substitutions in both positions F414 and V560, besides the two substitutions T30V and I94V, possess significantly increased mediator-activity for electron mediators other than oxygen when compared to GOx-T30V; I94V. Suitable amino acids for the substitutions are all remaining nineteen (19) proteinogenic amino acids. In particular, suitable amino acids are Arg, Asn, Asp, Cys, Gly, His, Ile, Leu, Met, Ser, Thr, Tyr and Val for position F414, and Ala, Ile, Leu, Met, Pro, Thr, Tyr and Val for position V560.

In some instances, the positions A173 and A332, besides the two substitutions T30V and I94V, can lead to an increase in GOx activity when compared to GOx-WT and GOx-T30V; I94V. Suitable amino acids for the substitutions are all remaining nineteen (19) proteinogenic amino acids. In particular, suitable amino acids are Ile, Thr and Val for position A173, and Ser and Asn for position A332.

This disclosure thus enables one of skill in the art to obtain GOx variants having significantly reduced oxygen consumption rates. In addition, this disclosure enables one of skill in the art to obtain GOx variants having significantly reduced oxygen consumption rates and/or significantly increased mediator-activity for certain electron mediators other than oxygen, either individually or for both features in combination via specific amino acid substitution(s).

These and other advantages, effects, features and objects of the inventive concept will become better understood from the description that follows. The description of exemplary embodiments is not intended to limit the inventive concept to the particular forms disclosed, but on the contrary, the intention is to cover all modifications, equivalents and alternatives falling within the spirit and scope of the inventive concept as defined by the embodiments above and the claims below. Reference should therefore be made to the embodiments above and claims below for interpreting the scope of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIG. 8 shows residual activity of GOx-WT, GOx-T30V; I94V and GOx variant EZ07 on different sugars when compared to glucose. For determining residual activities, the mediator assay for characterization was applied as described in the Materials and Methods section under item ff). The substrate concentration was 181.8 mM in the reaction mixtures.

FIG. 9 shows enzyme parameters for GOx-WT, GOx-T30V; I94V and GOx variant EZ07. The parameters were calculated according to Michaelis-Menten kinetics applying the least square method in Microsoft® Excel®. For the activity determination, the mediator assay for characterization was applied as described in the Materials and Methods section under item ff).

Figure 1:
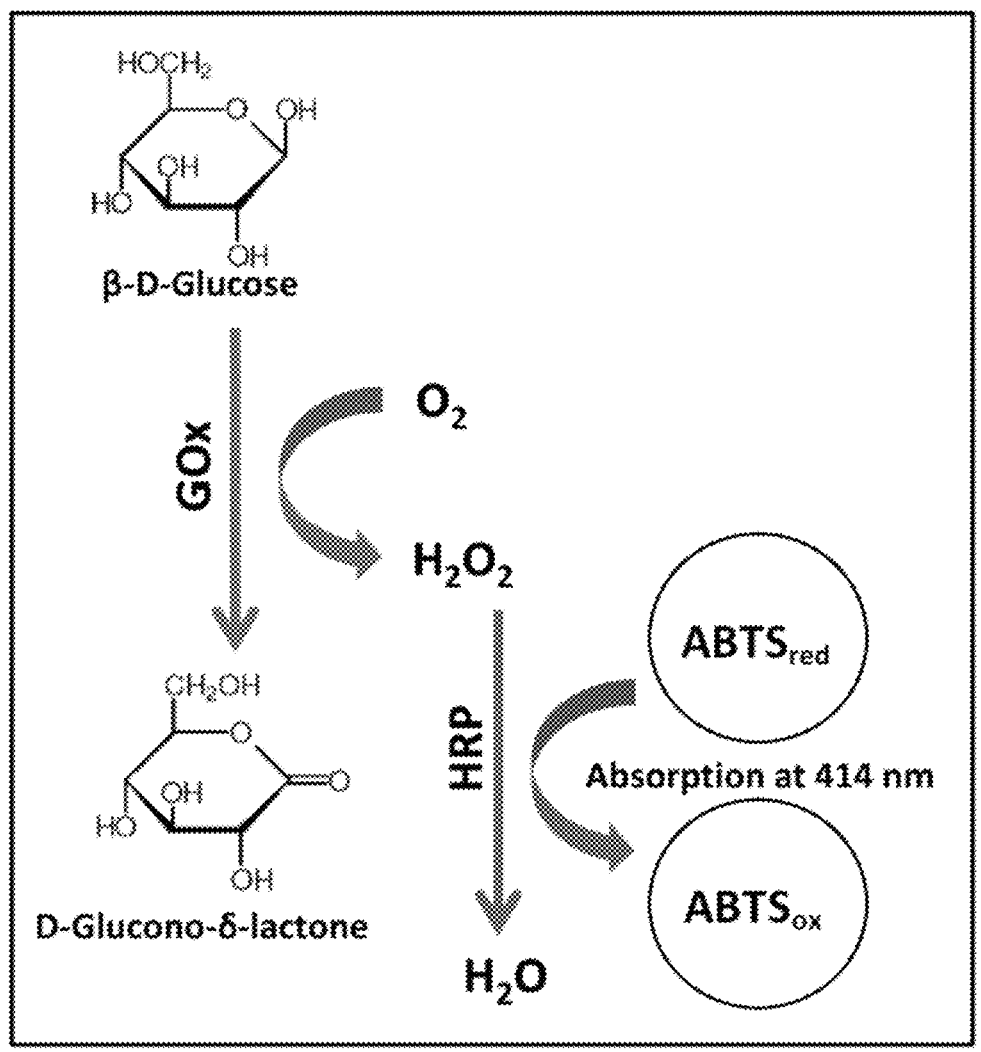
FIG. 1 shows a principle of an activity determination on oxygen for the GOx variants herein. The $H_2O_2$ produced during the reductive half reaction of GOx and horseradish peroxidase (HRP) is used to oxidize the chromogenic substrate ABTS. The color change of ABTS is monitored by absorption at 414 nm. This principle forms the basis of the ABTS assay as outlined in the Materials and Methods section under item gg).

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DETAILED DESCRIPTION

Overview

Persons with diabetes are in need of accurate blood glucose measurements during their everyday life. As outlined above, existing enzymatic measurement systems are based on oxygen-dependent GOxs and GDHs that are unspecific for glucose.

In GOx-WT from *A. niger*, the oxidase activity is about three to four times higher than its dehydrogenase activity. Accordingly, when dissolved oxygen is present in a blood-glucose assay system, the electrons generated during oxidation of the substrate glucose also can be transferred to the oxygen. Thus, the enzyme activity measured in the presence of an electron mediator may be affected by the dissolved oxygen concentration. However, GOx-WT from *A. niger* is specific for glucose and exhibits sufficient temperature stability.

By contrast, the GDH(s) are resistant to dissolved oxygen in the blood samples but are not sufficiently specific for glucose, and thus may be affected by other sugar types present in a blood sample such as, for example, maltose, galactose, xylose and maltotriose.

As noted above, it is an object of this disclosure to eliminate the effects of dissolved oxygen during blood-glucose measurements based on GOxs while preserving and further increasing its advantageous properties. Thus, GOx variants are provided herein having oxidase activity that is significantly reduced when compared to GOx-WT and GOx-T30V; I94V according to SEQ ID NO:1, while at the same time having dehydrogenase activity that is significantly increased when compared to GOx-WT and GOx-T30V; I94V.

An inventive concept herein is based upon an unexpected and surprising finding of specific GOx variants exhibit improved properties over known GOxs in the field of blood glucose measurements (i.e., maintaining its specificity for the substrate glucose and significantly reducing the oxygen consumption rates via a shift from oxidase activity towards dehydrogenase activity and/or having an increased activity for specific electron mediators other than oxygen).

To prove the GOx properties of the GOx variants herein, most available activity assays unfortunately could not be relied upon to indicate a reduction of molecular oxygen to $H_2O_2$. Specifically, for mediated electron transfer, Zhu et al. (2006, 2007), supra, established a product-based GOx detection assay (hereinafter CODA). That assay indeed allows for the oxygen-independent detection of gluconolactone, but still in the presence of oxygen, it is not possible to detect specifically the mediated electron transfer by mediators other than oxygen, which is highly relevant in case of real-time blood glucose analytic devices.

Definitions

As used herein, "activity" or "enzyme activity" of a glucose oxidase or of the GOx variants herein means a measure of its ability to catalyze the oxidation reaction D-glucose+oxygen→gluconolactone+$H_2O_2$, and may be expressed as the rate at which the product of the reaction is produced. For example, glucose oxidase activity can be represented as the amount of product (gluconolactone and/or $H_2O_2$) produced per unit of time, or per unit (e.g., concentration or weight) of glucose oxidase.

As used herein, "accept certain electron mediators other than oxygen for electron transfer" means a capability of the GOx variants herein to interact with and thus accept mediators selected from: nitrosoanilines and derivatives thereof, azo-compounds, phenazines and derivatives thereof, phenothiazines and derivatives thereof, phenoxazines and derivatives thereof, ferrocenes and derivatives thereof, potassium ferricyanide, Ru- and Os-complexes, quinones and derivatives thereof, indophenols, viologens, tetrathiafulvalene and derivatives thereof, and phthalocyanines for mediated electron transfer. More specifically, the electron mediator or mediator other than oxygen can be selected from: quinones, such as phenanthrendiones, 1,4 diamino anthraquinone and metallcomplexes of phenanthrendione, and nitrosoanilines, such as N,N-bis(2-hydroxyethyl)-4-nitrosoaniline or N,N-bis(2-hydroxyethyl)-2-methoxy-4-nitrosoaniline. Either of the latter two nitrosoanilines will hereinafter be referred to as "nitrosoaniline mediator". Examples of such electron mediators are described in, for example, U.S. Pat. Nos. 5,393,615; 5,498,542; 5,520,786; as well as, Int'l Patent Application Publication Nos. WO 2009/129108 and WO 93/25898; US Patent Application Publication No. 2009/0095642; JP Patent Application Publication No. 57-128678; EP Patent Application Publication No. 0 441 222; and Prevoteau et al. (2010) *Electrochem. Comm.* 12:213-215; and Berchmans et al. (2003) *Mater. Chem. Phys.* 77:390-396. In some instances, the electron mediators are fast reduced by $FADH_2$ but slow or not reduced by ascorbic acids; such mediators are derivatives of 2-[4-(dimethylamino)phenyl]-diazenecarboxamide.

As used herein, "additional modification(s) in the amino acid sequence" and "additional amino acid substitution(s)" mean a substitution of at least one amino acid by any of the remaining nineteen (19) proteinogenic amino acids in any of positions S53; A137; A173; A332; F414 and V560 according to SEQ ID NO:1. Further, the above expressions encompass cooperative amino acid substitutions by any of the remaining nineteen (19) proteinogenic amino acids or chemical equivalents thereof, provided that at least two, three, four, five or even six positions are substituted in any of positions selected from: S53; A137; A173; A332; F414 and V560 according to SEQ ID NO:1.

As used herein, "certain immobilized mediator" means an electron mediator or mediator other than oxygen selected from: nitrosoanilines and derivatives thereof, azo-compounds, phenazines and derivatives thereof, phenothiazines and derivatives thereof, phenoxazines and derivatives thereof, ferrocenes and derivatives thereof, potassium ferricyanide, Ru- and Os-complexes, quinones and derivatives thereof, indophenols, viologens, tetrathiafulvalene and derivatives thereof, and phthalocyanines.

As used herein, "dehydrogenase activity" means an enzymatic activity of the GOx variants herein to catalyze oxidation of glucose to generate gluconolactone by utilizing an electron mediator other than oxygen as an electron acceptor. Dehydrogenase activity may be assayed by measuring the amount of electrons transferred to the used mediator other than oxygen. Dehydrogenase activity additionally can mean a mole amount of the substrate (glucose) oxidized per unit time measured by the amount of electrons transferred to the mediator other than oxygen at 25° C. in 10 mM PPB (pH 7.0), 0.6 mM methoxy PMS (mPMS).

As used herein, "electron mediator(s)" and "mediator(s) other than oxygen" denote a small organic or inorganic chemical capable of existing in both, an oxidized and a reduced form, and that reacts quickly to donate or receive electrons. Specifically, electron mediator(s) and mediator(s) other than oxygen can mean small organic or inorganic chemicals, being an electron acceptor for glucose and thereby being converted from the oxidized into the reduced form. Following this, the mediator delivers the electrons in the reduced form to a working electrode for either electrochemical glucose measurement or to an indicator molecule for colorimetric measurement in a blood glucose assay system. Some electron acceptors act as an indicator molecule by itself and can be used directly for colorimetric measurement of glucose.

As used herein, "enzyme" means any substance composed wholly or largely of protein or polypeptides that catalyzes or promotes, more or less specifically, one or more chemical or biochemical reaction(s). Enzyme can also refer to a catalytic polynucleotide (e.g., RNA or DNA).

As used herein, "enzyme activity" means, in relation to the GOx variants herein, a protein that catalyzes the oxidation of beta-D-glucose into D-glucono-1,5-lactone (D-glucose+oxygen→gluconolactone+$H_2O_2$), which then may hydrolyze to gluconic acid.

As used herein, "enzyme specificity for glucose" or "specific for glucose" means activity of the GOx variants herein for the substrate glucose of >99.5%, >99.9% or even 100% when determined by the mediator assay as outlined in the Material and Methods under item ff). By implication, the residual activity of the GOx variants herein for sugars other than glucose such as galactose, maltose, xylose and maltotriose is <6% when determined by the mediator assay as outlined in the Material and Methods section under item ff).

As used herein, "glucose oxidase(s)" means a protein that catalyzes the oxidation of beta-D-glucose into D-glucono-1,5-lactone (D-glucose+oxygen→gluconolactone+$H_2O_2$), which then may be hydrolyzed to gluconic acid. Accordingly, glucose oxidases are an enzyme. Further, "a polypeptide having the activity of a glucose oxidase" means a polypeptide having the afore-mentioned activity. Glucose oxidase(s) may be abbreviated by "GOx(s)" or "E.C. 1.1.3.4." "Glucose oxidase" is thus a member of the class of oxidation enzymes, which catalyzes an oxidation reaction, by adding, inserting, contributing or transferring oxygen from a source or donor to a substrate. Such enzymes also are called oxidoreductases or redox enzymes, and encompass oxygenases, hydrogenases or reductases, oxidases and peroxidases.

As used herein "GOx-WT or WT" means wild-type GOx of the fungus *A. niger*. The GOx-WT of *A. niger* includes the natural sequence of amino acids according to SEQ ID NO:2.

As used herein, "GOx-T30V; I94V" means a GOx based on the wild-type *A. niger* wild-type (WT) sequence according the SEQ ID NO:2, further having the two substitutions T30V and I94V in its polypeptide sequence (i.e., SEQ ID NO:1). "GOx double-mutant" as used herein equally denotes a GOx-based on the *A. niger* WT sequence according the SEQ ID NO:2, further having the two substitutions T30V and I94V in its polypeptide sequence (i.e., GOx double-mutant is derived from Zhu et al. (2006, 2007), supra). Likewise, "GOx-T30V; I94V" or "T30VI94V" or "double-mutant" or "parent-mutant" means a GOx variant having the two substitutions T30V and I94V according to SEQ ID NO:1 as described in Zhu et al. (2006, 2007), supra.

Accordingly, the "parent mutant" or "double-mutant" means a GOx polypeptide from which any other herein provided GOx polypeptide is derived or made from, using any methods, tools or techniques described herein. The "parent mutant" or "double-mutant" is the polypeptide according to SEQ ID NO:1. Consequently, a "parent polynucleotide" is one that encodes a parent polypeptide (i.e., the polynucleotide according to SEQ ID NO:10 for GOx-T30V; I94V).

The GOx variant(s) herein all have in common the two substitutions T30V and I94V according to SEQ ID NO:1, and at least one additional amino acid substitution at any of the position(s) S53; A137; A173; A332; F414 and V560 by one of the remaining nineteen (19) proteinogenic amino acids suitable for replacement herein. Respective "EZ" numbers may abbreviate the GOx variant(s) herein, where "EZ" stands for enzyme.

As used herein, "modified" or "modification," with respect to the GOx variants herein, means to a GOx containing besides the two amino acid substitutions T30V and I94V according to SEQ ID NO:1, at least one additional amino acid substitution in the polypeptide sequence according to SEQ ID NO:1, at any of the position(s) S53; A137; A173; A332; F414 and V560. The term(s) also mean the respective polynucleotide or sequence-conservative variations thereof encoding such a "modified" GOx variant.

As used herein, "mutation" or "variation" or "modification" means any detectable change in genetic material (e.g., DNA or RNA) or any process, mechanism or result of such a change. This includes gene mutations, in which the structure (e.g., DNA or RNA sequence) of a gene is altered, any gene or DNA or RNA arising from any mutation process, and any expression product (e.g., protein or polynucleotide) expressed by a modified gene or DNA sequence. Such changes also include changes in the promoter, ribosome-binding site, etc. Relatedly, the polypeptide(s) herein also may be referred to as being a "mutant," "mutein," "variant," "modified GOx" or "modification" meaning that it has been made, altered, derived or is in some way different or changed from GOx-WT of *A. niger* itself, and from GOx-T30V; I94V according to SEQ ID NO:1.

As used herein, "oxidation reaction" means in general terms a chemical or biochemical reaction involving the addition of oxygen to a substrate, to form an oxygenated or oxidized substrate or product. An oxidation reaction is typically accompanied by a reduction reaction (hence the term "redox" reaction encompasses both, oxidation and reduction). A compound is "oxidized" when it receives oxygen or loses electrons. A compound is "reduced" when it loses oxygen or gains electrons. GOxs typically catalyze the oxidation of a primary alcohol group to an aldehyde. More specifically, "oxidase activity" means an enzymatic activity of the GOx variants herein to catalyze oxidation of glucose to generate gluconolactone with utilizing oxygen as an electron acceptor. Oxidase activity may be assayed by measuring an amount of generated $H_2O_2$ by any methods known in the art. For example, oxidase activity may be assayed by reagents for $H_2O_2$ detection, such as 4AA/TODB/POD (4-aminoantipyrine(N,N-Bis(4-sulfobutyl)-3-methylalanine disodium salt/horseradish peroxidase) or by Pt electrode. Oxidase activity additionally can mean a mole amount of the substrate (glucose) oxidized per unit time measured by the amount of generated $H_2O_2$ at 25° C. in 10 mM PPB, pH 7.0, 1.5 mM TODB, 2 U/mL HRP, and 1.5 mM 4-aminoantipyrine (4AA). The formation of quinoneimine dye may be measured spectrophotometrically at 546 nm.

As used herein, "oxygen donor," "oxidizing agent" and "oxidant" mean a substance, molecule or compound that donates oxygen to a substrate in an oxidation reaction. Typically, the oxygen donor is reduced (accepts electrons). Exemplary oxygen donors include, but are not limited to, molecular oxygen (O) or dioxygen ($O_2$), and peroxides, which include alkyl peroxides such as t-butyl peroxide and $H_2O_2$. Peroxide(s) is any compound(s) having two oxygen atoms bound to each other.

As used herein, "oxygen-dependent" and "oxygen-dependency" mean a GOx activity characterized by residual oxygen activity >30% when determined by the ABTS assay as outlined in the Materials and Methods section under item gg). In contrast, "oxygen-independent" and "oxygen-independency" mean a GOx activity characterized by residual oxygen activity ≤30%, <25%, <20%, <15% or even <10%, when determined by the ABTS assay as outlined in the Materials and Methods section under item gg).

As used herein, "RNA molecule" means a linear polymer of ribonucleotide molecules, which is single-stranded and serves as a template for protein synthesis of the GOx variants herein according to the SEQ ID N0:3 to SEQ ID N0:9.

As used herein, "sequence-conservative variations" of a polynucleotide sequence mean those in which a change of one or more nucleotides in a given codon position results in no alteration in the amino acid encoded at that position.

As used herein, "significantly increased mediator activity" or "significantly increased activity for electron mediators other than oxygen" means a GOx activity characterized by at least a 1.5-fold increased activity for electron mediators other than oxygen of that of the glucose oxidase according to SEQ ID NO:1 when determined by mediator assay as outlined in the Materials and Methods section under item ff).

As used herein, "significantly reduced oxygen activity" or "significantly reduced activity for oxygen as electron acceptor" means a GOx activity characterized by residual $O_2$ activity of ≤30%, <25%, <20%, <15% or even ≤10% when determined by the ABTS assay as outlined in the Materials and Methods section under item gg).

As used herein, "significantly reduced oxygen consumption rates" means a GOx variant herein having a residual oxygen content of >95% over a time period of 3 min when oxygen-dependency is determined indirectly by the oxidation of the chromogenic substrate ABTS as pursuant to the ABTS assay outlined in the Materials and Methods section under item gg).

As used herein, "specific for glucose or specific for the substrate glucose" means an activity of the GOx variants herein for the substrate glucose of 100% when determined by mediator assay as outlined in the Material and Methods section below. By implication, the residual activity of the herein provided GOxs for sugars other than glucose such as galactose, maltose, xylose and maltotriose is <6% when determined by mediator assay as outlined in the Material and Methods section under item ff).

As used herein, "tailor-made" means that a polypeptide sequence of the GOx variant herein enables it to interact with and thus accept electrons from a certain immobilized mediator.

As used herein, "unspecific for glucose" means a GOx activity for the substrate glucose of <100%, <99.9% or even <99.5%, when determined by mediator assay as outlined in the Material and Methods section under item ff). By implication, GOxs that are "unspecific for glucose" exhibit a GOx activity for sugars other than glucose such as galactose, maltose, xylose and maltotriose of >6%, when determined by mediator assay as outlined in the Material and Methods section under item ff).

Glucose Oxidase Variants and Compositions Based Thereupon

In one aspect, the inventive concept can be incorporated into a glucose oxidase according to SEQ ID NO:1 (a) having besides the two amino acid substitutions T30V and I94V, at least one additional amino acid substitution in any of the six (6) positions selected from: S53; A137; A173; A332; F414 and V560 in SEQ ID NO:1; or (b) a glucose oxidase that exhibits at least about 70%, at least about 80%, or even >90% amino acid sequence identity to the glucose oxidase according to (a), provided that the glucose oxidase of (b) has besides the two amino acid substitutions T30V and I94V, at least one (1) additional amino acid substitution in any of the six (6) positions selected from: S53; A137; A173; A332; F414 and V560 according to SEQ ID NO:1, and provided that the glucose oxidase according to (b) exhibits at least about 70%, at least about 80%, or even >90% of the enzyme activity of the glucose oxidase according to (a), and exhibits at least about 70%, at least about 80%, or even >90% of the enzyme specificity for glucose of the glucose oxidase according to (a), and provided that the glucose oxidase according to (b) exhibits at least a 5-fold reduced activity for oxygen as electron acceptor of the glucose oxidase according to SEQ ID NO:1 or exhibits at least a 1.5-fold increased activity for electron mediators other than oxygen of the glucose oxidase according to SEQ ID NO:1, or both; or (c) an active fragment of a glucose oxidase according to (a) or (b), provided that in the active fragment according to (c) the amino acid substitutions as outlined under (a) or (b) are preserved when compared to the glucose oxidase according to (a) or (b), and provided that the glucose oxidase according to (c) exhibits at least about 70%, at least about 80%, or even >90% of the enzyme activity of the glucose oxidase according to (a), and exhibits at least about 70%, at least about 80%, or even >90% of the enzyme specificity for glucose of the glucose oxidase according to (a), and provided that the glucose oxidase according to (c) exhibits at least about a 5-fold reduced activity for oxygen as electron acceptor of the glucose oxidase according to SEQ ID NO:1 or exhibits at least about a 1.5-fold increased activity for electron mediators other than oxygen of the glucose oxidase according to SEQ ID NO:1, or both.

In some instances, the GOx variants have, besides the two substitutions T30V and I94V according to SEQ ID NO:1, an additional two, or three, or four, or five, or six amino acid substitutions in any of the six (6) positions selected from the group S53; A137; A173; A332; F414 and V560 according to the SEQ ID NO:1.

In some instances, the amino acids for the additional substitution(s) are selected from: Ala, Arg, Asn, Asp, Cys, Gln, Glu, Gly, His, Ile, Leu, Lys, Met, Phe, Pro, Ser, Thr, Trp, Tyr and Val, provided that the substituent amino acid is other as present in the respective position according to SEQ ID NO:1.

In other instances, the amino acids for additional substitution(s) are selected from: Ala, Ile, Thr, Tyr, Val, Ser, Asn, Arg, Asp, Cys, Gly, His, Met, Leu, Phe, Met and Pro, provided that the substituent amino acid is other as present in the respective position according to SEQ ID NO:1.

In certain instances, the amino acids for additional substitution(s) are selected from: Phe for position S53; and/or Ser and Leu for position A137; and/or Ile, Thr and Val for position A173; and/or Ser, Asn and Val for position A332; and/or Arg, Asn, Asp, Cys, Gly, His, Ile, Met, Ser, Thr, Tyr and Val for position F414; and/or Ala, Ile, Leu, Met, Pro, Thr, Tyr and Val for position V560.

In another aspect, GOx variants are provided that have, besides the substitutions T30V and I94V according to the SEQ ID NO:1, at least one additional amino acid substitution in position(s) F414 and/or V560 combined with at least one amino acid substitution in the position(s) A137 and/or A173 and/or A332.

In another aspect, GOx variants (EZ07) are provided according to SEQ ID NO:3 that have, besides the substitutions T30V and I94V according to the SEQ ID NO:1, additional amino acid substitutions A173V; A332S; F414I and V560T.

In another aspect, GOx variants (EZ06) are provided according to SEQ ID NO:4 that have, besides the substitutions T30V and I94V according to the SEQ ID NO:1, additional amino acid substitutions A173I; A332S and F414L.

In another aspect, GOx variants (EZ10) are provided according to SEQ ID NO:6 that have, besides the substitutions T30V and I94V according to the SEQ ID NO:1, the additional amino acid substitutions A173V; A332N; F414V and V560L.

In another aspect, GOx variants are provided according to SEQ ID NO:3 to SEQ ID NO:9 that exhibit at least a mediator activity of 150% for the mediator N,N-bis(2-hydroxyethyl)-4-nitrosoaniline when compared to the respective mediator activity of GOx-T30V; I94V according to SEQ ID NO:1 when determined by the mediator assay as outlined in the Materials and Methods section under item ff).

In some instances, GOx variants are provided having besides the two substitutions T30V and I94V according to SEQ ID NO:1, additional amino acid substitutions such as the following: (1) A173V; A332S; F414Y and V560A or (2) A173V; A332S and F414Y, which exhibit at least a mediator activity of 150% for the mediator N,N-bis(2-hydroxyethyl)-2-methoxy-4-nitrosoaniline when compared to the respective mediator activity of GOx-T30V; I94V according to SEQ ID NO:1 when determined by the mediator assay as outlined in the Materials and Methods section under item ff).

The above substitutions (i.e., A173V; A332S; F414Y and V560A, or A173V; A332S and F414Y) in addition to the two substitutions T30V and I94V according to SEQ ID NO:1, reflect another characteristic of the GOx variants herein, namely the capability to accept certain electron mediators other than $O_2$ for electron transfer, in this case the N,N-bis(2-hydroxyethyl)-2-methoxy-4-nitrosoaniline mediator.

In another aspect, GOx variants are provided where the activity for oxygen as electron acceptor is determined by an ABTS assay having the steps of: (a) 75 µL of sample enzyme solution are transferred to a 96-well flat-bottom microplate containing 100 µL of phosphate buffer (pH 7); (b) 20 µL of reaction mixture is added to each well resulting in the following concentrations: 0.91 U/mL HRP; 2.3 mM ABTS (2,2'-azino-bis(3-ethylbenzothiazoline-6-sulphonic acid)); (c) the reactions starts by adding 25 µL glucose substrate solution and subsequent shaking of the plate at 1000 rpm for 30 sec; and (d) the oxidation of ABTS is kinetically determined at 414 nm using a microplate reader, where the activity for electron mediators other than oxygen is determined by a mediator assay having the steps of: (a) 75 µL sample of enzyme solution is transferred to a 96-well flat-bottom microplate; (b) 100 µL of mediator solution (19.05 mM N,N-bis(2-hydroxyethyl)-4-nitrosoaniline); 5% (w/w) polyvinylpyrrolidone, pH 7 and 20 µL of 25 mM phosphomolybdic acid are added; (c) the reaction starts by adding 25 µL glucose substrate solution and subsequent shaking of the plate at 1000 rpm for 1 min; (d) the kinetic of phosphomolybdic acid reduction is monitored at 700 nm using a microplate-reader.

In another aspect, GOx variants are provided that have an at least 5-fold reduced activity for oxygen as electron acceptor when compared to wild-type GOx of *A. niger* and/or when compared to a GOx according to SEQ ID NO:1 by means of the ABTS assay having the steps of: (a) 75 µL of sample enzyme solution are transferred to a 96-well flat-bottom microplate containing 100 µL of phosphate buffer (pH 7); (b) 20 µL of reaction mixture is added to each well resulting in the following concentrations: 0.91 U/mL HRP; 2.3 mM ABTS (2,2'-azino-bis(3-ethylbenzothiazoline-6-sulphonic acid)); (c) the reactions starts by adding 25 µL glucose substrate solution and subsequent shaking of the plate at 1000 rpm for 30 sec; and (d) the oxidation of ABTS is kinetically determined at 414 nm using a microplate reader.

In another aspect, GOx variants are provided that exhibit an at least 1.5-fold increased activity for mediators other than oxygen when compared to a GOx according to SEQ ID NO:1, when determined by mediator assay having the steps of: (a 75 µL sample of enzyme solution is transferred to a 96-well flat-bottom microplate; (b) 100 µL of mediator solution (19.05 mM N,N-bis(2-hydroxyethyl)-4-nitrosoaniline); 5% (w/w) polyvinylpyrrolidone, pH 7 and 20 µL of 25 mM phosphomolybdic acid are added; (c) the reaction starts by adding 25 µL glucose substrate solution and subsequent shaking of the plate at 1000 rpm for 1 min; and (d) the kinetic of phosphomolybdic acid reduction is monitored at 700 nm using a microplate-reader.

In another aspect, GOx variants are provided that exhibit a glucose specificity of at least about 99.9% and/or a galactose specificity <4% and/or a maltose specificity <0.3% and/or a xylose specificity <6% and/or a maltotriose <0.1%, when determined by a mediator assay having the steps of: (a). 75 µL sample of enzyme solution is transferred to a 96-well flat-bottom microplate; (b) 100 µL of mediator solution (19.05 mM N,N-bis(2-hydroxyethyl)-4-nitrosoaniline); 5% (w/w) polyvinylpyrrolidone, pH 7 and 20 µL of 25 mM phosphomolybdic acid are added; (c) the reaction starts by adding 25 µL of the respective sugar substrate solution and subsequent shaking of the plate at 1000 rpm for 1 min; and (d) the kinetic of phosphomolybdic acid reduction is monitored at 700 nm using a microplate-reader.

In another aspect, GOx variants are provided that exhibit an activity of >400%, >500% or even >600% for nitrosoaniline mediator for electron transfer when compared to the nitrosoaniline mediator activity of GOx according to SEQ ID NO:1 by means of mediator assay having the steps of: (a) 75 µL sample of enzyme solution is transferred to a 96-well flat-bottom microplate; (b) 100 µL of mediator solution (19.05 mM N,N-bis(2-hydroxyethyl)-4-nitrosoaniline); 5% (w/w) polyvinylpyrrolidone, pH 7 and 20 µL of 25 mM phosphomolybdic acid are added; (c) the reaction starts by adding 25 µL glucose substrate solution and subsequent shaking of the plate at 1000 rpm for 1 min; and (d) the kinetic of phosphomolybdic acid reduction is monitored at 700 nm using a microplate-reader. Additionally, the GOx variants exhibit an oxygen activity of ≤30%, <25%, <20%, <15%, or even ≤10% when compared to the oxygen activity of GOx according to SEQ ID NO:1 by means of ABTS assay having the steps of: (a) 75 µL of sample enzyme solution are transferred to a 96-well flat-bottom microplate containing 100 µL of phosphate buffer (pH 7); (b) 20 µL of reaction mixture is added to each well resulting in the following concentrations: 0.91 U/mL HRP; 2.3 mM ABTS (2,2'-azino-bis(3-ethylbenzothiazoline-6-sulphonic acid)); (c) the reactions starts by adding 25 µL glucose substrate solution and subsequent shaking of the plate at 1000 rpm for 30 sec; and (d) the oxidation of ABTS is kinetically determined at 414 nm using a microplate reader.

In another aspect, an isolated polynucleotide encoding GOx variants herein are provided. In other instances, an active (i.e., functional) equivalent/fragment of the GOx variants herein are provided. As used herein, "active equivalent(s)/fragment(s) thereof" or synonymous "functional equivalent(s)/fragment(s) thereof" mean any modified and thus optimized GOx variant herein, whereby at least one amino acid is missing or substituted by another amino acid as in the corresponding sequence according to SEQ ID NO:1, with the proviso that such equivalent(s)/fragment(s) still exhibit the essential properties as regards enzyme activity, enzyme specificity and the significantly reduced oxygen consumption rates and/or significantly increased activity for specific mediators other than oxygen, by having present at least the substitutions T30V and I94V according to SEQ ID NO:1, and further having at least one additional amino acid substitution in any of the positions selected from: S53; A137; A173; A332; F414 and V560 according to SEQ ID NO:1.

In certain instances, the functional equivalent(s)/fragment(s) of the GOx variants herein encompass amino acid sequence(s) being at least about 70% homologous, at least about 80% homologous or even >90% homologous to the sequences according to the SEQ ID NO:2 to SEQ ID NO:9.

In another aspect, expression vectors are provided that include at least one isolated polynucleotide encoding a GOx variant herein or an active fragment thereof.

In another aspect, a host cell is provided that includes an expression vector containing the isolated polynucleotide encoding at least one GOx variant or an active fragment thereof, also referred to as transformant.

In some instances, the vector includes all or a part of one of the DNA sequences encoding for a GOx variant herein.

Suitable expression vectors containing the desired coding and control sequences of the GOx variants herein may be constructed using standard recombinant DNA techniques known in the art, many of which are described in Sambrook et al. (1989), supra.

Suitable host cells include, for example, *E. coli* HB101 (ATCC33694) available from Promega (Madison, Wis., USA), XL1-Blue MRF' available from Stratagene (La Jolla, Calif., USA) and the like. Suitable *Pichia* host cells include, for example, *P. pastoris* X33 or *P. pastoris* KM71H available from Invitrogen (Carlsbad, Calif. 92008, USA)

In another aspect, methods are provided for producing a GOx variant or an active fragment thereof, where the methods include culturing the above-described transformant. Is some instance, the methods are used to obtain GOx variants or an active fragment.

The recombinant production of the GOx variants herein may be conducted in host cells known in the art. Suitable host cells include, but are not limited to, strains of filamentous fungi such as, for example, *A. niger, A. sojae* and *A. oryyzae*, as well as strains of yeast such as, for example, *P. pastoris, S. cerevisiae* and *H. polymorpha*. In certain instances, the GOx variants or functional equivalents herein are obtainable by expression of a polynucleotide encoding the GOx variants or fragments in *S. cerevisiae*.

Expression vectors may be introduced into host cells by any method known in the art. For example, transformation of host cells with expression vectors can be carried out by polyethylene glycol-mediated protoplast transformation method (see, Sambrook et al. (1989), supra). However, other methods can be employed for introducing expression vectors into host cells such as, for example, electroporation, ballistic DNA injection, or protoplast fusion.

Once an expression vector encoding a GOx variant herein has been introduced into an appropriate host cell, the host cell may be cultured under conditions permitting expression of the desired GOx variant. Host cells containing the desired expression vector (and thus bearing the DNA sequence encoding for the GOx variants herein) can be easily identified by antibiotic selection or complementation of auxotrophic mutants and selection from minimal medium. See, e.g., Sambrook & Russell "Molecular Cloning: a laboratory manual" (3$^{rd}$ ed., Cold Spring Harbor, N.Y. 2001).

The expression of the GOx variants can be identified by different methods such as measuring production of GOx mRNA transcripts, detecting the gene product immunologically or detecting enzymatic activity of the gene product. In particular, an enzymatic assay should be applied as outlined under the mediator assay in the Materials and Methods section under item ff). In addition, the GOx variants herein can be identified by the significantly reduced oxygen consumption rates when determined by the ABTS assay as outlined in the Materials and Methods section set out under item gg).

In other instances, the GOx variants can be produced by in vitro translation of the mRNA encoded by a DNA sequence encoding for one of the GOx variants herein. For example, the DNA sequences may be inserted into a suitable expression vector, which in turn may be used in an in vitro transcription/translation system.

The expression vector therefore can include an isolated polynucleotide as described above operably linked to a promoter sequence capable of promoting its expression in a cell-free peptide synthesis system.

The polypeptides produced by such methods may then be isolated and purified using various routine protein purification techniques. For example, chromatographic procedures such as ion exchange chromatography, gel filtration chromatography and affinity chromatography may be employed.

In another aspect, pharmaceutical compositions are provided that include at least one GOx variant herein or an active fragment thereof.

Advantageously, the GOx variants herein retain their inherent property to be specific for the substrate glucose, but due to the at least one additional amino acid substitution in the amino acid sequence in specific positions besides the substitutions T30V and I94V according to SEQ ID NO:1, the maximal residual oxygen activity is reduced to ≤30% when determined by the ABTS assay as outlined in the Materials and Methods section under item gg). Concomitantly, the GOx variants herein exhibit an enzyme activity of >400%, >500% or even >600% for electron mediators other than oxygen when determined by mediator assay as outlined in the Materials and Methods section below under item ff).

Methods

In one aspect, the inventive concept can be incorporated into methods of detecting, determining or measuring glucose in an ex vivo body fluid sample by a GOx variant herein or an active fragment thereof, where the detecting, determining or measuring includes the step of contacting an ex vivo body fluid sample with the GOx variant or an active fragment thereof.

In some instances, the detecting, determining or measuring of glucose is performed using a test element such as a biosensor or a test strip device.

In another aspect, methods are provided for producing the GOx variants herein, to nucleic acids encoding the GOx variants, to vectors, host cells.

In another aspect, methods are provided for generating tailor-made oxygen-independent GOx variants adapted to an immobilized mediator. The mediators can be selected from: nitrosoanilines, especially β-nitrosoanilines or derivatives thereof, and in particular the nitrosoaniline mediators or derivatives thereof is/are preferred as electron mediators in accordance with the disclosure. In general, mediators from the group of nitrosoanilines react in situ is on a test strip with glucose and the GOx to form a species that acts as electron mediator. Nitrosoanilines with the context of glucose measurements and mediator activity are described in detail in Hones et al. (2008) *Diabetes Technol. Therap.* 10:10-26; and EP Patent Application Publication No. 0 354 441. This listing should be not limited to mediators other than oxygen in accordance with this disclosure as other commercially available electron mediators known to one of skill in the art are fully encompassed for use herein.

Devices and Kits

In one aspect, the inventive concept can be incorporated into devices including at least one GOx variant herein. In some instances, the device is for assaying glucose in a body fluid sample, and thus includes at least one of the GOx variants herein and an electron mediator other than oxygen.

In some instances, the GOx variant has, besides the two substitutions T30V and I94V according to the SEQ ID NO:1, at least one additional amino acid substitution in any of the four (4) positions selected: A173; A332; F414 and V560 of the SEQ ID NO:1. Likewise, and as noted above, the electron mediator or mediator other than oxygen can be a nitrosoaniline and derivatives thereof, azo-compounds, phenazines and derivatives thereof, phenothiazines and derivatives thereof, phenoxazines and derivatives thereof, ferrocenes and derivatives thereof, potassium ferricyanide, Ru- and Os-complexes, quinones and derivatives thereof.

One of the major applications of the GOx variants herein is their use in test elements to monitor the blood-glucose level in ex vivo body fluid samples of persons with diabetes. Of course many kinds of samples may be investigated. In particular, bodily fluids like blood, serum, and plasma are the sources for such samples.

In another aspect, enzyme electrodes are provided that include at least one of the GOx variants herein immobilized on an electrode.

In another aspect, enzyme sensors are provided for assaying glucose that include the enzyme electrode as a working electrode, and thus bearing at least one of the GOx variants herein.

In yet another aspect, kits are provided for assaying glucose in a body fluid sample that includes at least one of the GOx variants herein and an electron mediator other than oxygen. In addition, the kits can include a buffer necessary for measuring an appropriate electron mediator other than oxygen, such as nitrosoaniline mediator, and, if necessary, enzymes such as peroxidases, as well as a standard solution of glucose for preparing a calibration curve and an instruction for use.

With respect to these devices, the concentration of the glucose in a sample may be determined by measuring the amount of electrons generated by the enzyme reaction. Various sensor systems are known in the art, including carbon electrodes, metal electrodes, and platinum electrodes. The GOx variants herein are immobilized on the electrode. Examples of the means for immobilizing include cross-linking, encapsulating into a macromolecular matrix, coating with a dialysis membrane, optical cross-linking polymer, electroconductive polymer, oxidation-reduction polymer, and any combination thereof.

Likewise, the devices may have a similar structure as any of conventional, commercially available electrochemical biosensor test strips for monitoring blood glucose levels. For example, such a device can have two electrodes (e.g., a working electrode and a reference/counter electrode) positioned on an insulating substrate, a reagent port and a sample receiver. The reagent port includes the GOx variant and the mediator other than oxygen. When a sample, such as blood sample, is added to the sample receiver, glucose contained in the sample will react with the GOx variant, thereby the electron transfer is indicative for the amount of glucose in the sample. Typical examples of electrochemical sensors suited for the determination of enzyme substrates are known from, for example, Int'l Patent Application Publication No. WO 2004/113900 and U.S. Pat. No. 5,997,817.

As an alternative to electrochemical biosensors, optical detection technologies might be used. Typically, such optical devices are based on color changes that occur in a reagent system comprising the GOx variant, an electron mediator and an indicator. The color changes can be quantified using fluorescence, absorption or remission measurements. Typical examples of optical devices suited for determining enzyme substrates are known from, for example, U.S. Pat. Nos. 7,008,799; 6,036,919 and 5,334,508.

SUMMARY

In view of the above, this disclosure combines in the GOx variants the following advantageous features: (1) the glucose specificity properties of GOxs; (2) with the oxygen-independent enzyme activity properties of GDHs via a shift from oxidase activity towards dehydrogenase activity; and (3) optionally an increased activity for certain electron mediators other than oxygen, for achieving accurate glucose measurements, in particular accurate blood glucose measurements.

As used herein, "shift from oxidase activity towards dehydrogenase activity" means: (1) a decrease in oxygen activity starting from 1.0 of the GOx-T30V; I94V as reference towards ≤0.3, <0.25, <0.2, <0.15, or even ≤0.1 residual oxygen activity of the GOx variants herein when determined by the ABTS assay as outlined in the Materials and Methods sections under item gg); and (2) a concomitant increase in dehydrogenase activity starting from a mediator activity 1.0 of the GOx-T30V; I94V as reference towards at least 1.5 mediator activity of the GOx variants herein when determined by the mediator assay as outlined in the Materials and Methods section under item ff).

The above values represent the ratio (quotient) between the enzyme activity of the GOx variants herein in terms of oxygen activity and mediator activity, and the respective enzyme activity of GOx-T30V; I94V as references. The ratio (quotient) is based on both GOx activities (oxygen activity and mediator activity in [U/mg]) when determined by ELISA as outlined in the Materials and Methods section under item ee.

Each of the nucleic acid molecules according to SEQ ID NO:11 to SEQ ID NO:17 encode a modified polypeptide or fragment thereof, which is derived from SEQ ID NO:10 (GOx-T30V; I94V) encoding a polypeptide according to SEQ ID NO:1 (i.e., GOx-T30V; I94V).

Pursuant to this disclosure, the nucleic acid molecule corresponding to SEQ ID NO:1 (i.e., SEQ ID NO:10) was used to further improve the kinetic properties of the GOx enzyme, characterized by a shift from oxidase activity towards dehydrogenase activity. This was achieved via specific nucleotide sequence modifications resulting in amino acid substitutions in at least one of positions S53; A137; A173; A332; F414 and V560, whereas the two substitutions T30V and I94V have been already present according to SEQ ID NO:1.

In another aspect, GOx variants are provided that have, besides the two substitutions T30V and I94V according to SEQ ID NO:1, an additional two, three, four, five or six amino acid substitutions in any of the six positions selected from: S53; A137; A173; A332; F414; and V560 of SEQ ID NO:1, thereby exhibiting cooperative effects on the GOx enzyme activity.

As used herein, "cooperative effects on GOx enzyme activity" means at least two additional amino acid substitutions in any of the positions S53; A137; A173; A332; F414 and V560 besides the two substitutions T30V and I94V according to SEQ ID NO:1, having effects on GOx enzyme activity in terms of decreasing the GOx oxygen consumption rate. Moreover, cooperative effects on GOx enzyme activity can mean at least two additional amino acid substitutions in any of the positions S53; A137; A173; A332; F414 and V560 besides the two substitutions T30V and I94V according to SEQ ID NO:1, having effects on GOx enzyme activity in terms of decreasing the GOx oxygen consumption rate and/or increasing the GOx mediator activity for electron mediators other than oxygen. Furthermore, cooperative effects on GOx enzyme activity can mean at least two additional amino acid substitutions in any of the positions S53; A137; A173; A332; F414 and V560 besides the two substitutions T30V and I94V according to SEQ ID NO:1, having effects on GOx enzyme activity in terms of accepting certain electron mediators other than oxygen for electron transfer. In a specific aspect, GOx variants are provided having, besides the two amino acid substitutions T30V and I94V according to SEQ ID NO:1, additional amino acid substitutions in the positions F414 and V560 by any of the remaining nineteen (19) proteinogenic amino acids, combined with amino acid substitutions in the positions A137; A173 and A332 by any of the remaining nineteen (19) proteinogenic amino acids.

In a specific aspect, GOx variants are provided having, besides the two amino acid substitutions T30V and I94V according to SEQ ID NO:1, additional combined amino acid substitutions in the positions F414 and V560 by any of the remaining nineteen (19) proteinogenic amino acids.

In a specific aspect, GOx variants are provided that have, besides the two amino acid substitutions T30V and I94V according to SEQ ID NO:1, the additional combined amino acid substitutions F414M or F414V and V560P or V560L.

In a specific aspect, GOx variants are provided that have, besides the two amino acid substitutions T30V and I94V according to SEQ ID NO:1, the additional amino acid substitutions F414M or F414V, combined with the amino acid substitution(s) V560P or V560L and/or A137L and/or A173I or A173V and/or A332S or A332V or A332T.

In a specific aspect, GOx variants are provided that have, besides the two amino acid substitutions T30V and I94V according to SEQ ID NO:1, the additional amino acid substitutions F414M or F414V, combined with the amino acid substitution(s) V560P or V560L and/or A137L and/or A173I or A173V and/or A332S or A332V or A332T.

In a specific aspect, GOx variants are provided that have, besides the two amino acid substitutions T30V and I94V according to SEQ ID NO:1, at least two combined amino acid substitutions selected from any of the above-mentioned substitutions.

In a specific aspect, GOx variants are provided that have a mediator activity of >400%, >450%, >500%, >550% or even >600% for the electron mediator N,N-bis(2-hydroxyethyl)-4-nitrosoaniline when determined by mediator assay as outlined in the Materials and Methods section under item ff).

In a specific aspect, GOx variants are provided that have an at least 5-fold reduced activity for oxygen as electron acceptor, or at least a 6-fold reduced activity for oxygen as electron acceptor, or at least a 7-fold reduced activity for oxygen as electron acceptor when compared to GOx-WT or when compared to GOx-T30V; I94V according to SEQ ID NO:1 by means of ABTS assay as outlined in the Materials and Methods section under item gg).

In another specific aspect, GOx variants are provided that have a remaining oxidase activity of ≤30% of that of GOx WT oxidase activity or of GOx-T30V; I94V oxidase activity according to SEQ ID NO:1, or alternatively having a remaining oxidase activity of <20% or <15% of that of GOx-WT oxidase activity or of GOx-T30V; I94V oxidase activity according to SEQ ID NO:1, or alternatively having a remaining oxidase activity of <10% of that of GOx-WT oxidase activity or of GOx-T30V; I94V oxidase activity according to SEQ ID NO:1, when determined by the ABTS assay as outlined in the Materials and Methods section under item gg).

In another aspect, functional equivalents/fragments of the nucleotide molecules as given in the SEQ ID NO:11 to SEQ ID NO:17 is a corresponding RNA molecule, which is encoded by the DNA sequence or a sequence being substantially complementary to the sequence of the SEQ ID NO:11 to SEQ ID NO:17.

In some instances, the degree or percentage of homology is at least about 70%, at least about 80%, at least about 90%, at least about 95%, at least about 99% or even 100% to the SEQ ID NO:3 to SEQ ID NO:9; provided that they exhibit the same substitutions as outlined throughout this disclosure and further exhibit essentially the same properties as the GOx variants herein, those essential properties being enzyme activity, enzyme specificity for glucose and the significantly reduced oxygen consumption rates and/or the significantly increased activity for specific mediators other than oxygen.

Sequence identity may be determined by the BLAST algorithm, the Basic Local Alignment Search Tool (BLAST) [Altschul et al. (1990) *J. Mol. Biol.* 215:403; and Altschul et al. (1997) *Nucleic Acids Res.* 25:3389-3402]. The herein mentioned percentages of amino acid sequence identity refer to determining sequence identity by the BLAST algorithm, where the region over which the homology is determined is the entire sequence of the GOx variants herein. Sequence identity may be determined by any other method known to one of skill in the art for purpose of sequence alignment and comparison.

One of skill in the art also understands that the GOx variants herein may have or may not have further modifications different from the before-mentioned substitutions without changing the essential properties of the GOx variants (i.e., specificity for glucose, the significantly reduced oxygen consumption rates and/or the significantly increased activity for specific mediators other than oxygen).

In another aspect, isolated polynucleotides are provided that encode a GOx variant herein or an active equivalent/fragment. The isolated polynucleotide may be a DNA or RNA molecule or a corresponding nucleic acid sequence thereof encoding for the following sequences as explicitly listed in the accompanying Sequence Listing (i.e., SEQ ID NO:11 to SEQ ID NO:17).

In another aspect, GOx variants are provided that exhibit temperature stability by having a residual enzyme activity of at least about 70% or at least about 80% in range of about 30° C. to about 47° C., when determined by a mediator assay as outlined in the Materials and Methods section under item ff). Alternatively, GOx variants are provided that exhibit temperature stability by having a residual enzyme activity of at least about 10% in a range of about 48° C. to about 60° C., when determined by a mediator assay as outlined in the Materials and Methods section under item ff).

The GOx variants herein may be provided in various forms such as, for example, a freeze-dried reagent or as a solution in an appropriate storage solution.

The GOx variants herein are predominantly intended for application in more accurate diabetes blood-glucose testing devices. Specifically, the oxygen-independent GOx variants herein utilize oxygen for electron transfer only by significantly reduced oxygen consumption rates, this means the residual GOx activity for oxygen is ≤30%, <25%, <20%, <15% or even ≤10% when determined by the ABTS assay as outlined in the Materials and Methods section under item gg). Accordingly, the significant amount of glucose reacts in the mediator-related reaction for more adequate blood glucose measurements, whereas the reaction with the dissolved oxygen content in the blood sample is significantly reduced. This is beneficial to persons having diabetes when arterial, venous or capillary blood is the source for measurements or in case of measuring blood-glucose concentrations in different heights above sea level.

In another aspect, GOx variants are provided that exhibit significantly reduced oxygen consumption rates and/or significantly increased mediator activity for electron mediators other than oxygen, which also results in more accurate blood-glucose measurements persons with diabetes may benefits from.

EXAMPLES

The inventive concept will be more fully understood upon consideration of the following non-limiting examples, which are offered for purposes of illustration, not limitation.

In the examples below, all reagents, restriction enzymes, and other materials were obtained from Roche Diagnostics Germany, unless other commercial sources are specified, and used according to the instructions given by the suppliers. Operations and methods employed for the purification, characterization and cloning of DNA are well known in the art [Ausubel et al. (1994), supra] and can be adapted as required by one of skill in the art.

In the following examples, the inventors tested therefore specific GOx variants of the invention, separately for its mediated electron transfer, the electron transfer by oxygen and its glucose specificity to prove the core of the invention. Further, the properties in terms of thermostability were also tested.

The well-known ABTS assay was used herein [Sun et al. (2002) *Chembiochem* 3:781-783] to detect the activity of the GOx variants on oxygen. FIG. 1 shows the principle of the activity determination on oxygen.

Example 1: Testing for GOx Variants

Methods: To test the appropriate amino acid substitutions for its improvement on the GOx properties in terms of glucose specificity, reduced oxygen consumption rates and/or increased activity for specific mediators other than oxygen, specific GOx variants were tested (i) for its oxygen consumption rates (i.e., the enzymatic activity using oxygen as an electron acceptor in a colorimetric ABTS assay) and (ii) for mediated electron transfer by the nitrosoaniline mediator as exemplary mediator and (iii) for mediated electron transfer by nitrosoaniline mediator as exemplary mediator in the presence of different sugars as substrate (i.e., glucose, galactose, maltose, xylose, maltotriose).

Figure 2:
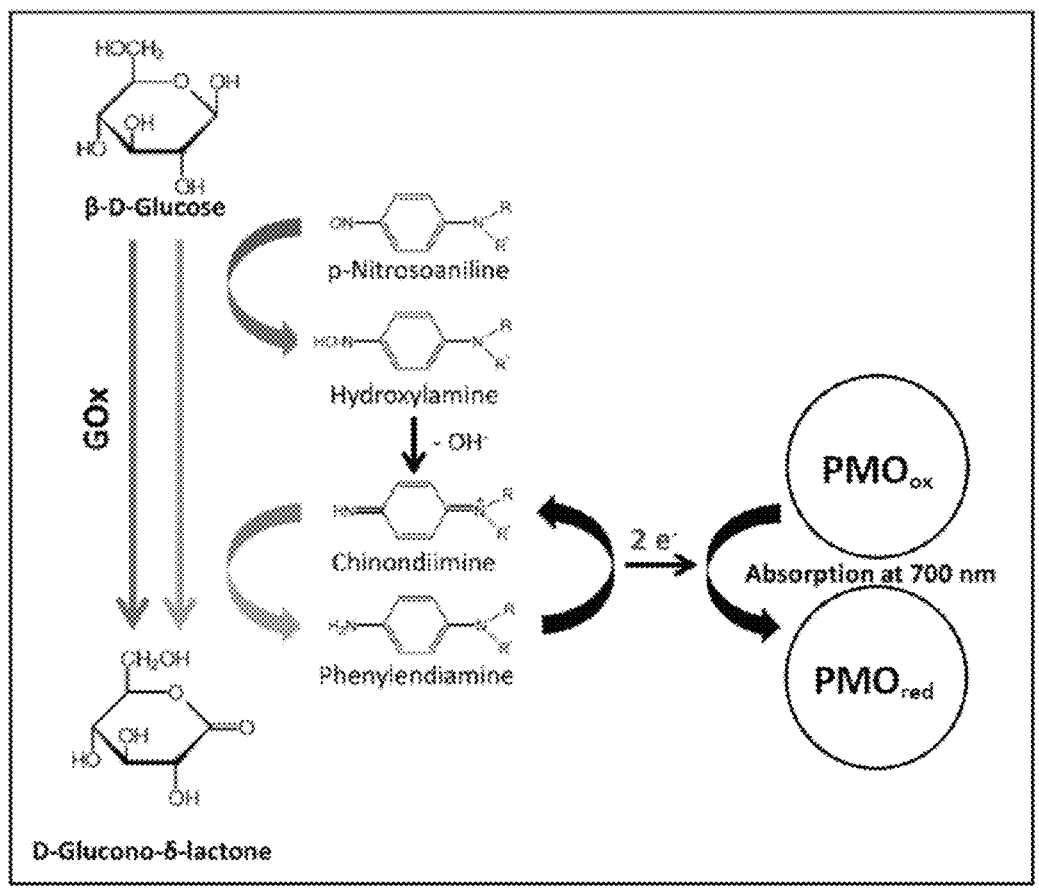
FIG. 2 depicts a mediator assay or phosphomolybdic acid (PMO) assay for detecting mediated electron transfer. The mediator compound gets reduced in two steps during the reductive half reaction of GOx. The mediator then transfers two electrons to the redox indicator PMO, which subsequently gets reduced. The color change of PMO during the reduction is monitored by absorption at 700 nm.

For the mediated electron transfer a p-nitrosonaniline compound was used [Becker (2005) "Die Glucose-Dye-Oxidoreduktase in der klinischen Diagnostik,". Dissertation thesis, Technische Universitat Kaiserslautern, Kaiserslautern]. FIG. 2 shows the principle of the mediator assay (i.e., a PMO (phosphomolybdic acid)-assay, in which the nitrosoaniline mediator N,N-bis(2-hydroxyethyl)-4-nitrosoaniline is applied.

In the above assay, two electrons, which come out of the mediator reaction, are transferred to the PMO, which subsequently is reduced. The color change from pale yellow, of the oxidised PMO, to dark blue, of the reduced PMO, was monitored by absorption at 700 nm.

To prove the specific GOx variants herein, the above-described mediator assay was adapted to low GOx activities in yeast cell supernatants that show a broad linear detection range from 0.65 U/L to 22 U/L in potassium phosphate buffer (0.2 M, pH 7.0). A standard deviation over a 96-well plate of 10.2% was reached under said conditions. For the calculation of the standard deviation the background was considered by subtracting the values of the negative control (true standard deviation).

Glucose Oxidase Variants:

The double-mutant as described in Zhu et al. (2006, 2007), supra, was chosen as the starting material for the herein provided specific amino acid substitutions. This double-mutant has the following two substitutions: T30V and I94V inherently present (SEQ ID NO:1). GOx-T30V; I94V shows an improved thermal stability, an improved pH-stability, as well as an increased kcat value (69.5/s to 137.7/s)

A hypoglycosylating *Saccharomyces cerevisiae* strain was chosen as an expression host [Lehle et al. (1995) *FEBS Lett.* 370:41-45].

After cultivation of the cell clones that bear specific amino acid substitutions, the mediator assay and the ABTS-assay were applied in parallel. Clones, which showed increased mediator activity, reduced oxygen activity or both were selected for further investigation. Therefore, the selected clones and the controls were cultivated and screened 12 times. Subsequently, the GOx-genes of improved variants herein were isolated and sequenced. Afterwards, the genes of selected variants served as templates for further specific amino acid substitutions.

Figure 3:
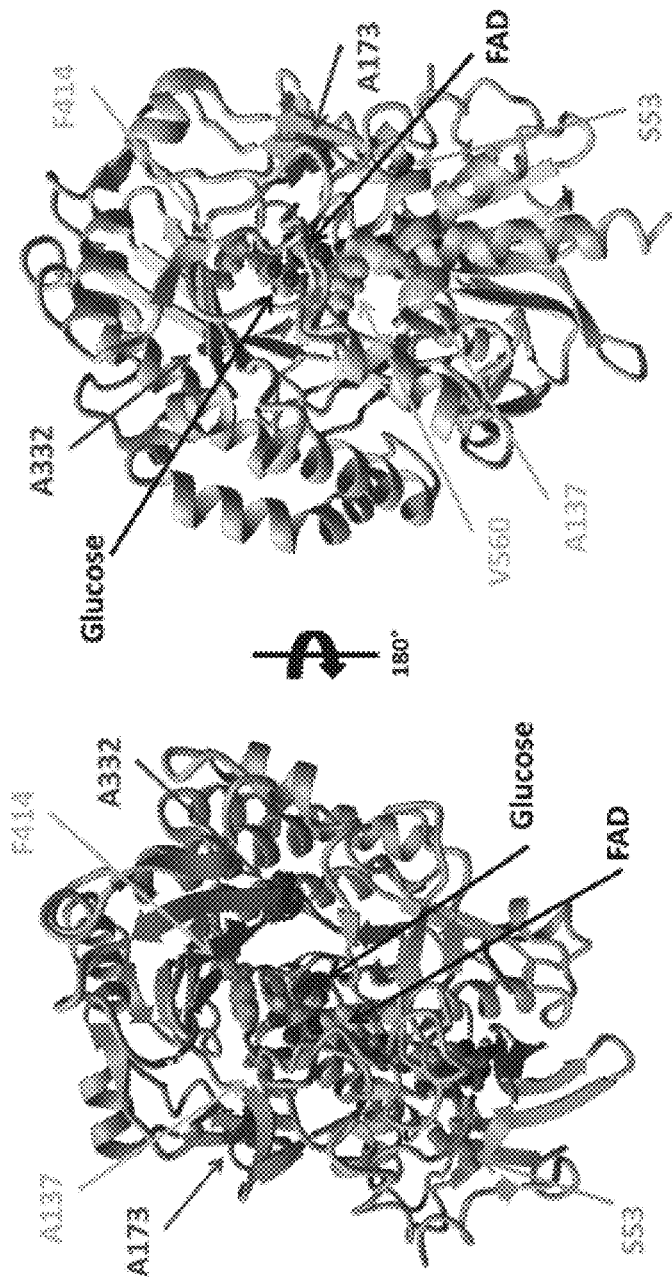
FIG. 3 shows a distinct location of the six (6) positions for amino acid substitutions in the protein structure pursuant to this disclosure.

Characterization of the Amino Acid Positions:

The specific amino acid positions were characterized of the GOx variants herein (i.e., S53; A137; A173; A332; F414; and V560). These positions are depicted in FIG. 3.

Pre-Characterization:

To further investigate specific GOx variants, a pre-characterization was performed, considering the following properties: (1) oxygen consumption; (2) specificity for glucose as substrate; (3) Michaelis-Menten kinetics (Mediator activity/glucose affinity); and (4) thermostability.

The cultivation of the corresponding cell clones took place in conventional shaking flasks. The supernatants were concentrated and buffered in 0.2 M potassium phosphate, pH 7.

(1) Oxygen consumption rate: The oxygen consumption was determined indirectly by the oxidation of the chromogenic substrate ABTS as outlined under item gg) in the below Materials and Methods section. To prove this data the oxygen consumption was measured directly using an optical oxygen probe. The GOx-variants were normalized to 2 U/L in the reaction approach.

(2) Specificity: As already outlined above, the GOx specificity for the substrate glucose plays a major role in the enzymatic glucose determination since there are clinical relevant sugars next to glucose, such as the four sugars galactose, maltose, xylose and maltoriose. Therefore, to prove specificity of the GOx variants herein, the sugars were chosen and compared to glucose. For these studies, the mediator assay was used, 181.8 mM of each sugar was applied.

(3) Mediator activity/glucose affinity: For a more detailed study on the mediator activity and for a determination of glucose affinity, tests were applied on the GOx variants for Michaelis-Menten kinetics.

(4) Thermostability: The thermostability of selected GOx variants herein was analyzed by applying the mediator assay as outlined in the Materials and Methods section under item ff). As additional controls, a hyper-glycosylated GOx, expressed in *A. niger* and the de-glycosylated GOx-WT were also analyzed.

Final Characterization of the GOx Variant, EZ07:

For final characterization, the respective EZ07-expressing *S. cerevsiae* strain was cultivated in a 10 L fermenter, the obtained EZ07 was subsequently purified. The purity of the final enzyme preparation was higher than 90% in 50 mM potassium phosphate buffer pH 7. Like in the pre-characterization phase the oxygen consumption, the specificity, the activity and the glucose affinity were studied. For the specific determination of GOx concentration, an ELISA was applied (see Material and Methods section under item ee).

The variant EZ07 also was characterized in terms of: 1a) oxygen consumption; 2a) specificity for glucose as substrate; 3a) Michaelis-Menten kinetics (mediator activity/glucose affinity); and 4a) thermostability.

1a) Oxygen consumption of EZ07: The measurement was implemented as described in 1). All tested enzymes (e.g., GOx-WT; GOx-T30V; I94V and EZ07) were purified a standard protocol as outlined in the Materials and Methods section under item dd) and adjusted to a protein concentration of 5 µg/mL.

The following oxygen consumption rates were detected [%/min]: GOx-WT: 17.44; GOx-T30V; I94V: 24.22; and EZ07: 3.86. The residual oxygen activity of EZ07 was 15.9% when compared to GOx-T30V; I94V and was 22.13% when compared to GOx-WT.

2a) Specificity of EZ07: The measurement was implemented as described in 2).

3a) Michaelis-Menten kinetics of EZ07: The measurement was implemented as described in 3).

4a) Thermostability: The measurement was implemented as described in 4).

Results:

Six (6) distinct amino acid positions S53; A137; A173; A332; F414 and V560, which are responsible for reduced oxygen consumption rates and/or increased mediator activity for mediators other than oxygen. Further, cooperative effects were found among the six (6) amino acid positions that enable one of skill in the art to design GOx variants in terms of glucose specificity, significantly reduced oxygen consumption rates, and/or increased activity for mediators other than oxygen.

In particular, it was found that positions V560 and F414, either alone or in combination, to be responsible for significantly reducing the oxygen consumption rates and/or being responsible for significantly increasing the mediator activity. In addition, the positions A173 and A332 were found to be responsible for both in combination a significant increase in mediator activity and concomitantly a significant reduction in oxygen consumption rates of the GOx variants herein. The positions S53 and A137 were found to be responsible for significantly increasing the mediator activity for specific mediators other than oxygen.

Further, it was found specific amino acids to be suitable for the GOx variants herein.

TABLE 1

An exemplary, suitable set of amino acids for the positions 173, 332, 414 and 560 and the corresponding degenerated codons.

| Residue | Reduced Set of Amino Acids | Degenerated Codons |
|---|---|---|
| 173 | AITV (SEQ ID NO: 42) | RYT |
| 332 | SN | ART |
| 414 | RNDCGHILFSTV (SEQ ID NO: 40) | NDT |
| 560 | AILMPTV (SEQ ID NO: 41) | VYK |

The specific activities of the tested GOx variants here are shown in Table 2 by a respective EZ numbering. The table is a comparison of the tested GOx variants herein with respect to mediator activity via the mediator assay and oxygen consumption properties via the ABTS assay.

The results are shown in the form of a ratio (quotient) between the GOx variants herein and the parent mutant (i.e., the GOx-T30V; I94V) as starting material. The results of the different microtiter-plates were comparable. The ratio is based on the specific activities [U/mg], determined by conventional ELISA technique as outlined in the Materials and Methods section under item ee). The table also shows the exact substitutions of the tested amino acid positions in accordance with this disclosure.

TABLE 2

Specific GOx variants herein with an EZ number code, tested for mediator activity and for (residual) oxygen activity.

| Gox Variant | A173 | A332 | A137 | F414 | V560 | S53 | Mediator Activity GOx Variant/ GOx-T30V; I94V | Oxygen Activity GOx Variant/ GOx-T30V; I94V |
|---|---|---|---|---|---|---|---|---|
| GOx-T30V; I94V (Reference) | — | — | — | — | — | — | 1.0 | 1.0 |
| EZ05 | — | S | — | — | A | — | 1.1 | 0.1 |
| EZ12 | — | S | — | — | — | F | 1.7 | 1.5 |
| EZ06 | I | S | — | L | — | — | 1.6 | 0.3 |
| EZ07 | V | S | — | I | T | — | 4.4 | 0.1 |
| EZ08 | V | N | — | — | P | — | 1.0 | 0.1 |

TABLE 2-continued

Specific GOx variants herein with an EZ number code, tested for mediator activity and for (residual) oxygen activity.

| Gox Variant | A173 | A332 | A137 | F414 | V560 | S53 | Mediator Activity GOx Variant/ GOx-T30V; I94V | Oxygen Activity GOx Variant/ GOx-T30V; I94V |
|---|---|---|---|---|---|---|---|---|
| EZ10 | V | N | — | V | L | — | 2.2 | 0.1 |
| EZ11 | — | S | — | — | P | — | 1.2 | 0.1 |
| EZ15 | — | — | L | — | — | — | 6.0 | 4.0 |

The results show that the different specific variants (EZ03, EZ05, EZ12, EZ06, EZ07, EZ08, EZ10, EZ11, EZ15) having the essential properties of reduced oxygen affinity leading to significantly reduced oxygen consumption rates and/or the increased mediator activity when compared to the parent mutant, GOx-T30V; I94V. The variants EZ03, EZ05, EZ07, EZ08, and EZ10 were undergoing further studies.

For instance, it was found that EZ07 (SEQ ID NO:3) and EZ10 (SEQ ID NO:6) both show significant improvements for increased mediator activity, as well as a significant decrease in the oxygen assay when compared to the parent mutant.

In particular, it was found that EZ07 was a significantly improved GOx variant without any limitation to the corresponding specific amino acid substitutions of the variant. Additionally, EZ07 shows a 4.4 times increase in the mediator assay when compared to the parent mutant and only a 0.1 times oxygen activity of the oxygen activity of the parent mutant in the ABTS-assay. In contrast, EZ12 (SEQ ID NO:8) and EZ15 (SEQ ID NO:9) showed concomitant increases for both, mediator and oxygen activities when compared to the parent mutant. EZ12 carries an additional substitution on position S53 when compared to the parent mutant (see, Table 2). Further, EZ15 was found to have a six-times increase in mediator activity due to the amino acid substitution A137L.

Example 2: Characterization of the Amino Acid Positions

Positions A173 and A332 are far away from the active site. A173 is a surface position; and A332 is located close to the substrate entrance channel. The two positions F414 and V560, which have an influence to the oxygen activity, are located close to the active site. F414 is above the glucose-binding site; and V560 sits next to glucose and FAD. Both of the two activity positions A137 and S53 are surface positions near the FAD.

Figure 4:
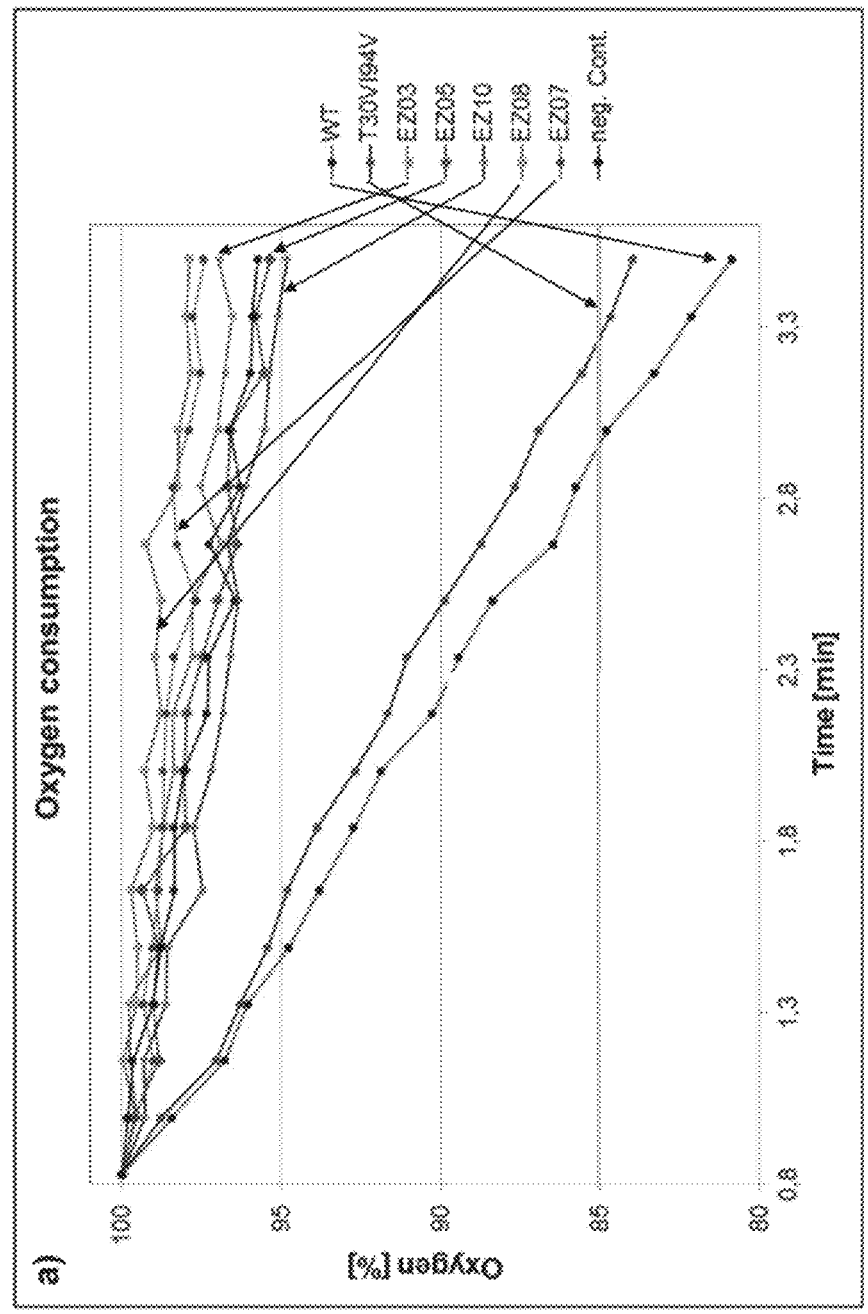
FIG. 4 shows oxygen consumption rates of different GOx-variants herein: (a) progression of the relative oxygen concentration as function of time; and (b) relative oxygen consumption rate per minute. The assay implementation is described in the Materials and Methods section under item hh). The enzymes were normalized to 2 U/L.
Figure 4:
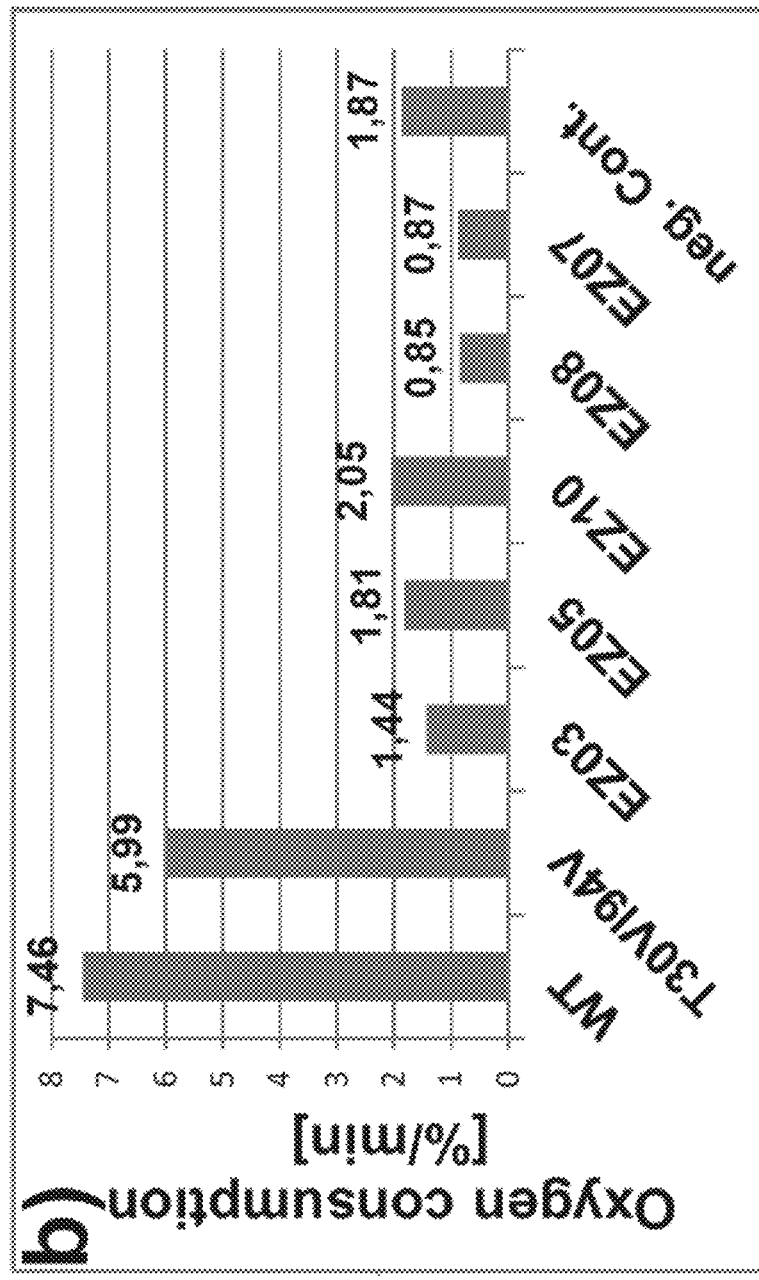

Pre-characterization:

The results for the selected pre-characterized variants are as follows:

1) Oxygen consumption rate: FIG. 4 shows progression of the oxygen content in the reaction mixture as a function of time (a) and the oxygen consumption rate per minute (b). As controls, GOx-T30V; I94V, GOx-WT and the supernatant of the negative control strain were analyzed.

GOx-WT and GOx-T30V; I94V show a similar behavior. Thus, all the tested GOx variants (EZ03, EZ05, EZ07, EZ08, EZ10) have a significantly reduced oxygen consumption rate. Moreover, as a surprising and unexpected finding, the tested variants cannot be clearly distinguished from the negative control, which indicates that the respective oxygen activities are even below the detection range of the assay under the selected conditions.

2) Specificity: Table 3 shows the residual GOx enzyme activities referring to glucose.

TABLE 3

Residual activity of GOx variants herein for different sugars. For determination of residual activities, the mediator assay for characterization was applied. The substrate concentration was 181.8 mM in the respective reaction mixtures. GOx-WT and GOx-T30V; I94V activities served as references.

| Residual activity [%] | Glucose | Galactose | Maltose | Xylose | Maltotriose |
|---|---|---|---|---|---|
| GOx-WT | 100 | 1.4 | 0 | 2.6 | 0 |
| GOx-T30V; I94V | 100 | 1.6 | 0 | 2.6 | 0 |
| EZ03 | 100 | 2.9 | 0 | 5.3 | 0 |
| EZ05 | 100 | 3.3 | 0.3 | 3.8 | 0 |
| EZ10 | 100 | 1.1 | 0 | 3.1 | 0 |
| EZ08 | 100 | 4.0 | 0.2 | 4.7 | 0 |
| EZ07 | 100 | 0 | 0 | 3.6 | 0 |

When compared to GOx-WT and the parent mutant GOx-T30V; I94V according to SEQ ID NO:1, none of the GOx variants herein showed significant interferences with maltose or maltotriose. EZ07 and EZ10 have the best results for all tested sugars.

Figure 5:
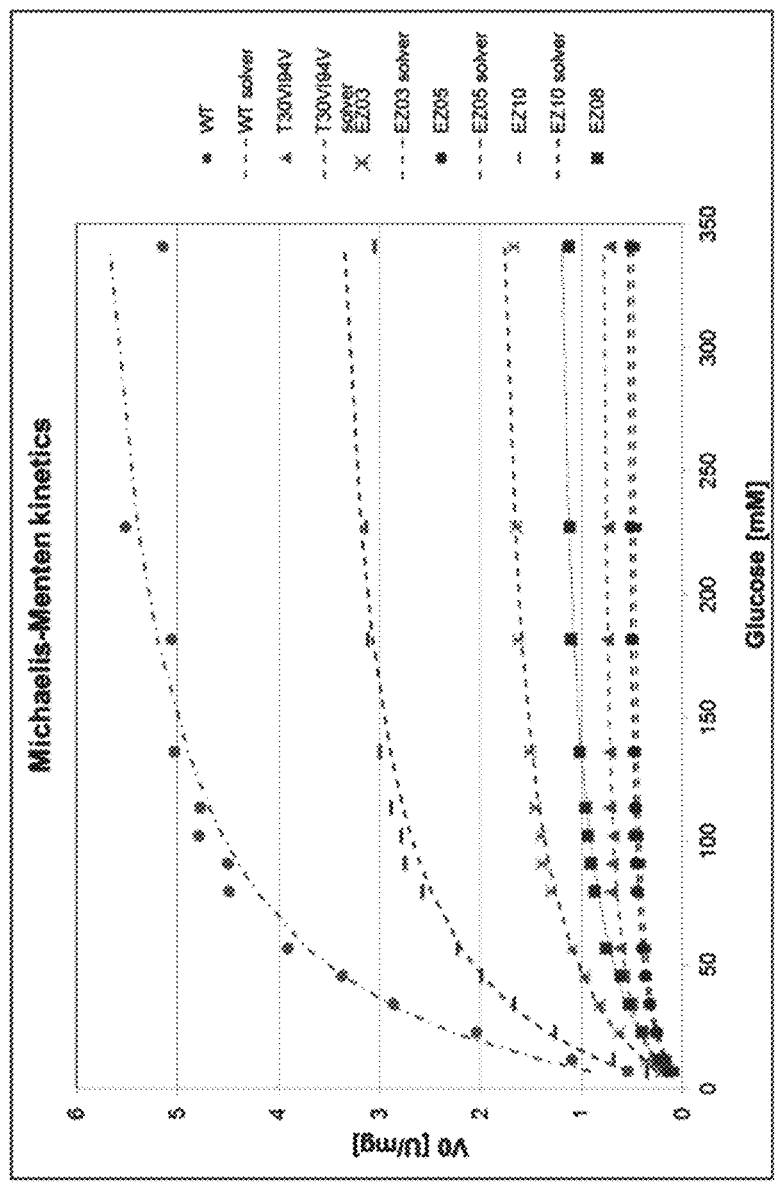
FIG. 5 depicts Michaelis-Menten kinetics of different GOx-variants herein. For the activity determination, the mediator assay for characterization was applied as outlined in the Material and Methods section under item ff). The dashed lines were calculated in Microsoft® Excel® applying the least square method.

3) Mediator activity/glucose affinity: The Michaelis-Menten kinetics are represented in FIG. 5. Table 4 shows the calculated values for $V_{max}$ and $K_M$.

TABLE 4

Enzyme parameters for different GOx-variants. The parameters were calculated according to Michaelis-Menten applying the least square method in Microsoft ® Excel ®.

| GOx Variant | $V_{max}$ | $K_M$ |
|---|---|---|
| GOx-WT | 0.53 | 25.90 |
| GOx-T30V; I94V | 0.83 | 21.84 |
| EZ03 | 2.00 | 46.62 |
| EZ05 | 0.57 | 24.83 |
| EZ07 | 6.35 | 40.26 |
| EZ08 | 1.37 | 49.69 |
| EZ10 | 3.75 | 40.14 |

Table 4 shows that EZ07 has at one hand an approximately 7.5 times higher $V_{max}$ value when compared to the parent mutant GOx-T30V; I94V, but on the other hand an almost two times higher $K_M$-value. However, the high $K_M$ value is a result of the high $V_{max}$ value. In FIG. 5, it can be clearly seen that the performance of EZ07 at low substrate concentrations is comparable to GOx-WT and the parent mutant GOx-T30V; I94V. EZ10 reached similar results but a lower $V_{max}$ value.

Figure 6:
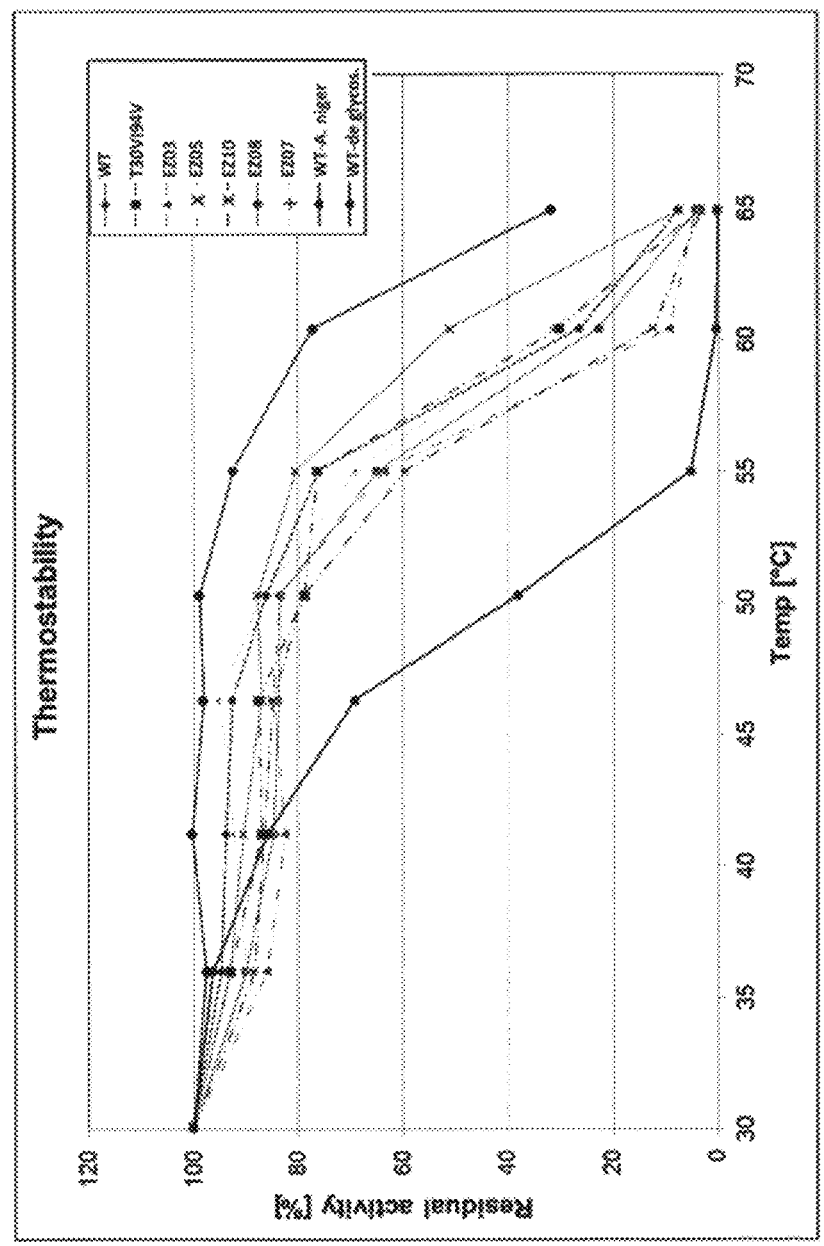
FIG. 6 shows thermostability properties of different GOx-variants herein. The assay was performed as outlined in the Material and Methods section under item ii). As additional controls de-glycosylated and hyper-glycosylated GOxs were used.

4) Thermostability: In FIG. 6, the residual activity is diagrammed for eight (8) different temperatures. The tested GOx variants herein, GOx-WT and GOx-T30V; I94V parent mutant show similar results. A significant drop down in the thermostability can be observed for the de-glycosylated GOx-WT; however, the hyper-glycosylated molecule shows a higher thermostability.

Conclusion:

In the specific testings 1) to 4) during all pre-characterization studies, EZ07 and EZ10 variant showed the most significant results. A significant drop down in the oxygen activity, as well as significant increase in the mediator activity, was achieved according to the pre-characterization results. The specificity of EZ07 and EZ10 are almost unchanged only a slight activity change on xylose was detected. Since the activity of EZ07 is approximately 1.7 times higher than the activity of EZ10, EZ07 was chosen for the final characterization.

It should be emphasized that the above results were generated using unpurified GOx variants herein. Accordingly, one of skill in the art is aware that the results may vary after using similar purified GOx variants. Also the specific protein determination in cell supernatants applying ELISA may be affected by impurities.

Example 3: Final Characterization of EZ07

For final characterization purified EZ07 variant was chosen.

Figure 7:
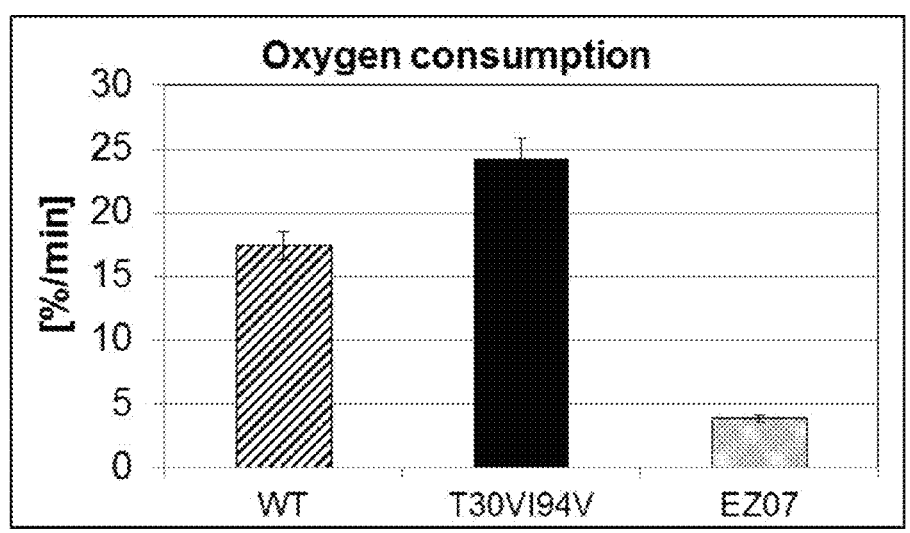
FIG. 7 shows relative oxygen consumption rates of GOx-WT, GOx-T30V; I94V and GOx-variant EZ07 (i.e., A173V; A332S; F414I and V560T, besides the substitutions T30V; I94V). The assay implementation is described the Materials and Methods section under item hh). The enzyme concentrations were normalized to 1.7 mg/L.

1a) Oxygen consumption EZ07: The relative oxygen consumption rate of the GOx-WT, GOx-T30V; I94V and EZ07 are depicted in FIG. 7. Under the selected conditions, the oxygen consumption rate of EZ07 is more than 10-fold reduced when compared to GOx-WT, which confirms the data of the pre-characterization study.

2a) Specificity of EZ07: FIG. 8 shows the residual activity of GOx-WT, GOx-T30V; I94V and EZ07 referring to glucose (100%). Specifically, FIG. 8 shows that there is no significant change in the specificity of EZ07 when compared to GOx-T30V; I94V and GOx-WT.

3a) Michaelis-Menten kinetics of EZ07: FIG. 9 compares the kinetics of GOx-WT, GOx-T30V; I94V and EZ07 in the mediator assay. According to FIG. 9, EZ07 shows 641.5% residual activity in the mediator assay and 17.5% residual activity in the ABTS assay when compared to GOx-WT, resulting in a 37 times reduced oxidase activity.

Figure 10:
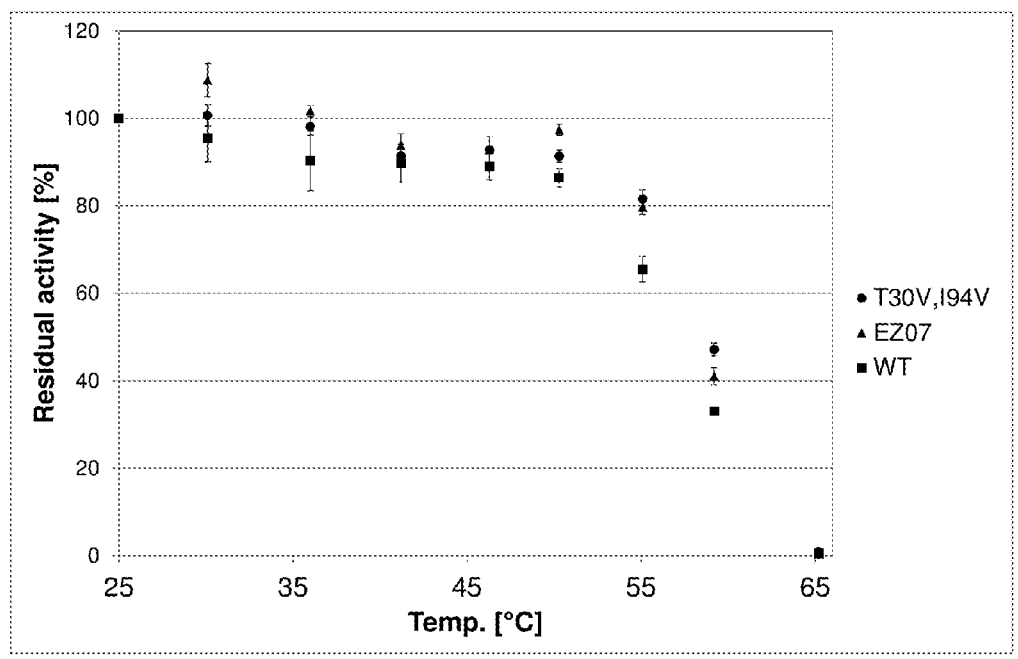
FIG. 10 shows residual activity of GOx-WT, GOx-T30V; I94V and GOx variant EZ07 after 15 min incubation at various temperatures between 25° C. and 67° C.

4a) Thermostability of EZ07: FIG. 10 indicates that the thermal stability of the GOx-EZ07 was maintained by the respective substitutions, when compared to the GOx-WT and the GOx-T30V; I94V.

Summary for the GOx Variants:

Six (6) amino acid positions were identified in the parent mutant GOx-T30V; I94V, which show effects on glucose specificity of the GOx variants herein, on enzyme activity for mediated electron transfer and on oxygen activity. All positions were saturated individually. To study cooperative effects positions clustered around the active site (S53; A137; A173; A332; F414; and V560) were saturated simultaneously. The most significant variants for improved mediator activity and/or reduced oxygen consumption rates when compared to the parent mutant properties were chosen for the pre-characterization. It turned out that EZ07 (having the additional substitutions A173V; A332S; F414I and V560T) shows the most significant results for the tested properties glucose specificity, mediator activity and oxygen consumption rates in the sense of this disclosure.

Thus, EZ07 was intensively studied for its mediator activity, oxidase activity, glucose specificity, as well as its thermal stability properties. The variant shows a 6.4-fold increase in specific activity for mediated electron transfer (GOx-WT: 7.4; EZ07: 47.5 U/mg) and a 5.7-fold reduced activity in the ABTS assay (GOx-WT: 451.1 U/mg; EZ07: 78.86 U/mg) resulting in a 36.5 times reduced oxidase activity. EZ07 has no significant changes in thermal stability or specificity.

Materials and Methods:

All chemicals were of analytical grade and purchased from Sigma-Aldrich (Taufkirchen, Germany), Applichem (Darmstadt, Germany) or Carl Roth (Karlsruhe, Germany). All enzymes were purchased from New England Biolabs (UK) and Sigma-Aldrich (Taufkirchen, Germany). The pYES2 shuttle vector and *Escherichia coli* strain DH5á were purchased from Invitrogen (Karlsruhe, Germany). The *S. cerevisiae* strain 7087 (ngd29mnn1) was provided by Roche Diagnostics [Lehle et al. (1995) *FEBS Lett.* 370:41-45]. DNA was quantified using a NanoDrop photometer (NanoDrop Technologies, Wilmington, Del., USA). Sequencing and oligonucleotide synthesis was done by Eurofins MWG Operon (Ebersberg, Germany). Primers used are mentioned in Table 5 (Supporting Information).

aa) Multiple- and single site saturation mutagenesis: For multiple site saturation mutagenesis, the Omnichange protocol was applied [Dennig et al. (2011) *PLoS ONE* 6:e26222]. 400 µl PCR reaction mixture contained 1 ng/µl of plasmid template, lx Phusion buffer (New England Biolabs, Frankfurt, Germany), 1 U of Phusion polymerase and 200 µM dNTP's. The reaction mixture was divided in four equal volumes and 250 nM of forward primer and reverse primers, targeting specific sites, were added for fragment amplifications. In the mixture for the vector backbone amplification, additional dNTP's were added to reach final concentration of 300 µM. For Fragment 1, targeting A173, primers P7 and P8 were added in the master mix. While for A332 saturation, P9 and P10 were used. F414 site was targeted by using P11 and P12. The V560 site was included in vector backbone as it was amplified by P13 and P14. The PCR program for amplification of fragments was 98° C. for 45 sec (1 cycle); 98° C. for 15 sec; 65° C. for 30 sec; 72° C. for 30 sec (20 cycles); 72° C. for 5 min (1 cycle).

For vector backbone amplification extension time of 4 min was applied. All fragments were column purified and the concentration was measured on NanoDrop photometer (NanoDrop Technologies, Wilmington, Del., USA). The PCR product was then subjected to overnight DpnI digestion (5 U each).

Digestion and Ligation of Fragments:

The concentration of insert fragments was adjusted to 0.06 pmol/µl. While vector backbone concentration was adjusted to 0.02 pmol/µl (dilution factor with DpnI digestion was also taken into consideration). 1 µl of cleavage solution (50% (500 mM Tris pH 9.0, 30% (100 mM Idodine in ethanol) and 20% dH$_2$O) was added to 4 µl of each fragment. The reaction was then incubated at 70° C. for 5 min. The cleaved fragments were mixed together and incubated at room temperature (RT) for 5 min before transformation of chemical competent *E. coli* DH5á for library amplification. For yeast transformation, the gene library was isolated from *E. coli* DH5á using the plasmid isolation kit "NucleoSpin® Plasmid" (MACHERY-NAGEL, Düren, Germany).

For individual site saturation mutagenesis (SSM) a two-step PCR protocol has been followed [Sambrook & Russel (2001), supra]. 50 µl PCR reaction mixture contained 1 ng/µl of plasmid template, 1× Phusion buffer (New England Biolabs, Frankfurt, Germany), 1 U of Phusion polymerase and 300 µM dNTP's. The reaction mixture was divided in two equal volumes, and 400 nM of forward primer and reverse primer of the targeted site were added to separate reaction mixtures. PCR program was 98° C. for 45 sec (1 cycle); 98° C. for 15 sec; 65° C. for 30 sec; 72° C. for 4 min (5 cycles); 72° C. for 5 min (1 cycle). After the first step, both reactions were pooled and the same program was carried out with 15 more repetitions for the amplifying cycles. The following primers were used: P15/P16 for position 173, P17/P18 for position 332, P19/P20 for position 414 and P21/22 for position 560. The PCR product was column purified and subsequently subjected for DpnI digestion.

bb) Gene Cloning and Yeast Cell Transformation:

The cloning of the mutated GOx-genes into the pYES2 vector backbone was performed according to a recombination mediated ligase free method [Oldenburg et al. (1997) *Nucleic Acids Res.* 25:451-452]. Firstly, 2 µg of pYES2-GOx-T30V, I94V double-mutant was linearized by SalI/BamHI digestion (10 U/µg DNA, 6 h, 37° C.) and subsequently purified by gel-extraction employing the NucleoSpin® Extract II—kit (MACHERY-NAGEL, Düren, Germany). The primers, used for library amplification, were designed in a way that the whole primer sequence is complementary to the linearized vector backbone.

Secondly, the linearized pYES2-vector and the amplified gene library were mixed in a ratio of 1:3 (250 ng/750 ng). This DNA-mix was used for the transformation of *S. cerevisiae* 7087 employing a lithium acetate method [Gietz & Schiestl (2007) *Nat. Protoc.* 2:31-34]. Transformants were grown on SC-U selective plates containing 2% glucose. For the transformation of circular plasmids 300 ng DNA was used.

cc) Cultivation and Expression in 96-Well Plates:

Single colonies grown on SC-U selective agar plates containing 2% glucose were transferred into 96-well microtiter plates (PS-F-bottom, greiner bio-one) containing 100 µL SC-U media (1% glucose) per well using toothpicks. The cultivation of the pre-culture took place in a plate shaker (Infors GmbH, Eisenach, Germany) under the following conditions: 900 rpm, 30° C., 70% humidity, 24 h. A certain amount of pre-culture was transferred from each well to 500 µL SC-U auto-induction media (0.5% glucose/2% galactose) in a deep well plate (riplate-rectangular, ritter). The main-culture was cultivated under the same conditions than the pre-culture, but for 72 h. Plates were centrifuged at 4000 rpm and RT for 20 min. The resultant supernatants were used for activity determinations.

dd) Production and purification of recombinant GOx:

Pre-cultivation: 500 mL SynY media (2% glucose) were inoculated to OD 600=0.2 using an overnight-culture of Sc7087/pYES2-GOx, the cultivations took place in 5 L shaking flasks for 12 h at 30° C. and 250 rpm. Main-cultivation: 10 L SynY media (1% glucose) was inoculated with 500 mL pre-culture. For the cultivation, a 10 L fermenter was used applying the following conditions: temperature: 30° C.; stirrer: 400 rpm; air flow: 1 vvm; time: 48 h.

Cell separation and buffer exchange: The GOx-containing supernatant was recovered by micro-filtration. For this purpose, the cross-flow filtration unit SartoJet (Sartorius Stedim Biotech GmbH, Göttingen, Germany) was used with one filter cassette (SARTOCON Slice, Hydrosart 0.45 µm, Sartorius Stedim Biotech GmbH, Göttingen, Germany). The feed pressure was adjusted to 2.0 bar, and the retentate pressure to 1.0 bar. The same filtration system was used for buffer exchange, and sample concentration applying a ultra-filtration cassette (SARTOCON Slice, Hydrosart 10 kDa, Sartorius Stedim Biotech GmbH, Göttingen, Germany) under the following conditions: buffer 50 mM $NaH_2PO_4$, pH 6; buffer exchange volumes: 7; feed pressure: 2.0 bar; retentate pressure: 1.0 bar; end volume 0.5 L.

For enzyme purification anion-exchange chromatography was applied, using the ÄKTA pilot system and a FinLine Pilot 35 column (GE Healthcare, Munich, Germany). The column was packed with 220 mL resin (Fractogel TSK DEAE-650s Merck), a flow rate of 62.5 cm/h was selected. Equilibration: 440 mL 50 mM sodium phosphate buffer pH6; sample load: 0.5 L retentate; wash: 440 mL 50 mM sodium phosphate buffer pH6; elution: 95% 50 mM sodium phosphate buffer pH6/5% 1M NaCl (step gradient). The GOx-containing fractions were pooled, subsequently a final buffer exchange against 50 mM potassium phosphate buffer pH 7 took place (Amicon® Ultracel-30k Millipore, Cork, Ireland).

ee) Normalization of Protein Concentrations:

An enzyme-linked immunosorbent assay (ELISA) was used for the specific determination of GOx concentrations. Each well of a streptavidin coated microtiter plate (Roche—Material No. 11643673001) was filled with 100 µL of the primary antibody solution (2 µg/mL; Rabbit PAK GOD-Biotin Acris R1083B), the plate was incubated for 1 h at room temperature. After a subsequent washing step (4 times 350 µL 9 g/L NaCl_0.1% Tween 20), 100 mL of enzyme sample was pipetted into the wells, followed by a second incubation step. The washing step was repeated and the plate was filled with 100 µL of the secondary antibody solution (10 µg/mL; Rabbit PAK GOD-HRP Acris R1083HRP). After a third incubation and washing step, the plate was filled with 100 µL of a $ABTS/H_2O$ solution (11684302001 Roche Diagnostics GmbH, Mannheim, Germany). The plate was incubated for 30 min at room temperature before the absorption at 405 nm was determined. Glucose oxidase from *A. niger* was used as internal standard (G7141-50KU SIGMA-ALDRICH).

ff) Mediator Assay:

For the liquid handling multi-channel pipettes from Brand (Transferpette S-8) and Eppendorf (Research pro) were used. 75 µL of sample (prepared supernatants/enzyme solution) were transferred to a 96-well flat-bottom microplate (greiner bio-one). 100 µL of mediator solution (19.05 mM N,N-bis(2-hydroxyethyl)-4-nitrosoaniline [Becker (2005), supra], Roche—Material No. 100088314; 5% (w/w) poly-vinylpyrrolidone, Roche—10003476964; pH 7) and 20 µL of 25 mM phosphomolybdic acid (Roche, Genisys-nr.: 11889893001) were added. The reactions were started by adding 25 µL substrate solution and subsequently shaking of the plate at 1000 rpm for 1 min. The kinetic of phosphomolybdic acid reduction was monitored at 700 nm using the microplate-reader Tecan Sunrise (Tecan Trading AG, Switzerland). For kinetic analysis Vmax and KM values were determined from initial velocity data plotted as a function of substrate concentrations with a linear correlation coefficient of >0.99.

gg) ABTS Assay:

For the liquid handling multi-channel pipettes from Brand (Transferpette S-8) and Eppendorf (Research pro) were used. 75 µL of sample (prepared supernatants/enzyme solution) were transferred to a 96-well flat-bottom microplate (greiner bio-one) containing 100 µL of phosphate buffer (pH 7). 20 µL of reaction mixture were added to each well resulting in the following concentrations: 0.91 U/mL HRP; 2.3 mM ABTS. The reactions were started by adding 25 µL substrate solution and subsequently shaking the plate at 1000 rpm for 30 sec. The oxidation of ABTS was kinetically determined at 414 nm using the microplate reader FLUOstar Omega (BMG LABTECH). For kinetic analysis $V_{max}$ and $K_M$ values were determined from initial velocity data plotted as a function of substrate concentrations with a linear correlation coefficient of >0.99.

hh) Oxygen Consumption Assay:

For the direct determination of the oxygen consumption the optical oxygen probe "Fibox3—Minisensor Oxygen Meter" (Precision Sensing GmbH, Regensburg, Germany) was used. The 1540 µL reaction mixture consisted of 840 µL phosphate buffer (0.2 M/pH 7), 175 µL substrate solution and 525 µL GOx-solution. The oxygen consumption (%/min) was kinetically determined.

ii) Thermal Stability:

100 µL of the enzyme solution were incubated at the corresponding temperature for 15 min and subsequently chilled on ice for 5 min. 75 µL were used for the activity determinations. The following temperatures were studied: 30-, 35-, 40-, 45-, 50-, 55-, 60-, and 65° C.

TABLE 5

Primers used in experimental section:

| Primer | Sequence |
|---|---|
| P1 | GGCGTGAATGTAAGCGTGACATA (SEQ ID NO: 18) |
| P2 | CACACTACCGCACTCCGTCGCCGGATCGGACTACTAGCAG (SEQ ID NO: 19) |
| P3 | CCGGATCGGACTACTAGCAG (SEQ ID NO: 20) |
| P4 | GTGTGATGGCGTGAGGCAGCGGCGTGAATGTAAGCGTGACATA (SEQ ID NO: 21) |
| P5 | GTGGTCTCCCTCGCTGCGGCCCTGCCACACTACATCAGGAGCAATGGCATTGAAGCCAG (SEQ ID NO: 22) |
| P6 | ATTACATGATGCGGCCCTCTAGATGCATGCTCGAGCGGCCGCCAGTGTGATGGATATCTG (SEQ ID NO: 23) |

TABLE 5 -continued

Primers used in experimental section:

| Primer | Sequence |
|---|---|
| P7 | GGTACTGTCCATRYTGGACCCCGCGACAC (SEQ ID NO: 24) |
| P8 | GGTGGTCTGGTCCTGCAGGTTCAAG (SEQ ID NO: 25) |
| P9 | GACCAGACCACCARTACCGTCCGCTCCC (SEQ ID NO: 26) |
| P10 | GAGTTCCGAGTACGCGACGTTGTGG (SEQ ID NO: 27) |
| P11 | TACTCGGAACTCNDTCTCGACACTGCC (SEQ ID NO: 28) |
| P12 | ATGGGACGACATTTGCGTAGGAGG (SEQ ID NO: 29) |
| P13 | ATGTCGTCCCATVYKATGACGGTGTTCTA (SEQ ID NO: 30) |
| P14 | ATGGACAGTACCATTAACACCATG (SEQ ID NO: 31) |
| P15 | GGTACTGTCCATNNKGGACCCCGCGACAC (SEQ ID NO: 32) |
| P16 | GTGTCGCGGGGTCCMNNATGGACAGTACC (SEQ ID NO: 33) |
| P17 | GACCAGACCACCNNKACCGTCCGCTCCC (SEQ ID NO: 34) |
| P18 | GGGAGCGGACGGTMNNGGTGGTCTGGTC (SEQ ID NO: 35) |
| P19 | TACTCGGAACTCNNKCTCGACACTGCC (SEQ ID NO: 36) |
| P20 | GGCAGTGTCGAGMNNGAGTTCCGAGTA (SEQ ID NO: 37) |
| P21 | ATGTCGTCCCATNNKATGACGGTGTTCTA (SEQ ID NO: 38) |
| P22 | TAGAACACCGTCATMNNATGGGACGACAT (SEQ ID NO: 39) |

The invention claimed is:

1. A glucose oxidase comprising:
(a) a glucose oxidase of SEQ ID NO:1 having amino acid substitutions T30V and I94V and at least one additional amino acid substitution selected from the group consisting of S53; A137; A173; A332; F414 and V560 in SEQ ID NO:1, wherein the glucose oxidase of (a) exhibits 30% or less activity for oxygen as an electron acceptor of the glucose oxidase of SEQ ID NO:1 or exhibits at least a 1.5-fold increased activity for electron mediators other than oxygen of the glucose oxidase of SEQ ID NO:1, or both;
(b) a glucose oxidase that exhibits at least 70% amino acid sequence identity to the glucose oxidase of (a), wherein the glucose oxidase of (b) also exhibits at least 70% of the enzyme activity of the glucose oxidase of (a), wherein the glucose oxidase of (b) exhibits at least 70% enzyme specificity for glucose of the glucose oxidase of (a), and wherein the glucose oxidase of (b) exhibits at least a 5-fold reduced activity for oxygen as an electron acceptor of the glucose oxidase of SEQ ID NO:1 or exhibits at least a 1.5-fold increased activity for electron mediators other than oxygen of the glucose oxidase of SEQ ID NO:1, or both; or
(c) an active fragment of the glucose oxidase of (a) or (b), wherein the active fragment of (c) has the amino acid substitutions in (a) or (b) that are preserved when compared to the glucose oxidase in (a) or (b), wherein the glucose oxidase of (c) exhibits at least 70%, of the enzyme activity of the glucose oxidase of (a), wherein the glucose oxidase of (c) exhibits at least 70% of the enzyme specificity for glucose of the glucose oxidase of (a), and wherein the glucose oxidase of (c) exhibits at least a 5-fold reduced activity for oxygen as an electron acceptor of the glucose oxidase of SEQ ID NO:1 or exhibits at least a 1.5-fold increased activity for electron mediators other than oxygen of the glucose oxidase of SEQ ID NO: 1, or both.

2. The glucose oxidase of claim 1, wherein activity for oxygen as the electron acceptor is determined by an azino-bis(3-ethylbenzothiazoline-6-sulphonic acid (ABTS) assay, wherein the assay comprises the steps of:
(1) transferring 75 µL of a sample enzyme solution to a 96-well flat-bottom microplate containing 100 µL of phosphate buffer (pH 7);
(2) adding 20 µL of reaction mixture to each well resulting in the following concentrations: 0.91 U/mL horseradish peroxidase (HRP); 2.3 mM ABTS;
(3) starting reactions by adding 25 µL of a glucose substrate solution and subsequent shaking the microplate at 1000 rpm for 30 sec; and
(4) kinetically determining oxidation of ABTS at 414 nm using a microplate reader,
wherein activity for electron mediators other than oxygen is determined by a mediator assay, and wherein the mediator assay comprises the steps of:
(1) transferring a 75 µL sample of the enzyme solution to a 96-well flat-bottom microplate;
(2) adding 100 µL of mediator solution (19.05 mM N,N-bis(2-hydroxyethyl)-4-nitrosoaniline); 5% (w/w) polyvinylpyrrolidone, pH 7 and 20 µL of 25 mM phosphomolybdic acid;
(3) starting a reaction by adding 25 µL glucose substrate solution and subsequent shaking of the microtiter plate at 1000 rpm for 1 min; and
(4) monitoring kinetic reduction of phosphomolybdic acid at 700 nm using a microplate reader.

3. The glucose oxidase of claim 1, wherein the electron mediators other than oxygen are selected from the group consisting of nitrosoanilines, azo-compounds, phenazines, phenothiazines, phenoxazines, ferrocenes, potassium ferricyanide, Ru- and Os-complexes, quinones, indophenols, viologens, tetrathiafulvalene, and phthalocyanines.

4. The glucose oxidase of claim 1, having substitutions T30V and I94V of SEQ ID NO:1 and additional two, three, four, five or six amino acid substitutions selected from the group consisting of S53; A137; A173; A332; F414 and V560 of SEQ ID NO:1.

5. The glucose oxidase of claim 1, wherein the amino acids for the additional substitution(s) are selected from the group consisting of Ala, Arg, Asn, Asp, Cys, Gln, Glu, Gly, His, Ile, Leu, Lys, Met, Phe, Pro, Ser, Thr, Trp, Tyr and Val, provided that the amino acid substitution is other than the one present in the respective position of SEQ ID NO:1.

6. A glucose oxidase of claim 1, wherein the amino acids for additional substitution(s) are selected from the group consisting of Phe for the position S53; and/or
Ser, Leu for the position A137; and/or
Ile, Thr, Val for the position A173; and/or
Ser, Asn, Val, Thr for the position A332; and/or
Arg, Asn, Asp, Cys, Gly, His, Ile, Met, Ser, Thr, Tyr, Val for the position F414; and/or
Ala, Ile, Leu, Met, Pro, Thr, Tyr, Val for the position V560.

7. The glucose oxidase of claim 1, wherein the at least one additional amino acid substitution is in position(s) F414 and/or V560 combined with at least one amino acid substitution in position(s) A137, A173 and/or A332.

8. The glucose oxidase of claim 1, wherein the at least one additional amino acid substitution is A173I; A332S and F414L.

9. The glucose oxidase of claim 1, wherein the at least one additional amino acid substitution is A173V; A332S; F414I and V560T.

10. The glucose oxidase of claim 1, wherein the at least one additional amino acid substitution is A173V; A332N; F414V and V560L.

11. The glucose oxidase of claim 1, exhibiting a glucose specificity of at least 99.9%, a galactose specificity of <4%, a maltose specificity of <0.3%, a xylose specificity of <6% and/or a maltotriose specificity of <0.1%, when determined by a mediator assay, comprising the steps of:

(1) transferring a 75 µL sample of enzyme solution to a 96-well flat-bottom microplate;
(2) adding 100 µL of mediator solution (19.05 mM N,N-bis(2-hydroxyethyl)-4-nitrosoaniline); 5% (w/w) polyvinylpyrrolidone, pH 7 and 20 µL of 25 mM phosphomolybdic acid;
(3) starting a reaction by adding 25 µL of the respective sugar substrate solution and subsequent shaking the microplate at 1000 rpm for 1 min;
(4) monitoring kinetic reduction of phosphomolybdic acid monitored at 700 nm using a microplate reader.

12. The glucose oxidase of claim 1, exhibiting an activity of >400%, >500% or >600% for a nitrosoaniline mediator for electron transfer when compared to nitrosoaniline mediator activity of the GOx according to SEQ ID NO:1 by a mediator assay, wherein the mediator assay comprises the steps of:

(1) transferring a 75 µL sample of enzyme solution to a 96-well flat-bottom microplate;
(2) adding 100 µL of mediator solution (19.05 mM N,N-bis(2-hydroxyethyl)-4-nitrosoaniline); 5% (w/w) polyvinylpyrrolidone, pH 7 and 20 µL of 25 mM phosphomolybdic acid;
(3) starting a reaction by adding 25 µL glucose substrate solution and subsequent shaking of the microplate at 1000 rpm for 1 min; and
(4) monitoring kinetic reduction of phosphomolybdic acid reduction at 700 nm using a microplate reader;

and an oxygen activity of ≤30% when compared to oxygen activity of the GOx according to SEQ ID NO:1 by means of an ABTS assay, the assay comprising the steps of:

(1) transferring 75 µL of a sample enzyme solution to a 96-well flat-bottom microplate containing 100 µL of phosphate buffer (pH 7);
(2) adding 20 µL of reaction mixture to each well resulting in the following concentrations: 0.91 U/mL horseradish peroxidase (HRP); 2.3 mM 2,2'-azino-bis(3-ethylbenzothiazoline-6-sulphonic acid (ABTS);
(3) starting reactions by adding 25 µL of a glucose substrate solution and subsequent shaking the microplate at 1000 rpm for 30 sec; and
(4) kinetically determining oxidation of ABTS at 414 nm using a microplate reader.

* * * * *

SEQUENCE LISTING

<160> NUMBER OF SEQ ID NOS: 41

<210> SEQ ID NO 1
<211> LENGTH: 583
<212> TYPE: PRT
<213> ORGANISM: Aspergillus niger

<400> SEQUENCE: 1

```
Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Gly Leu Val Gly Leu
            20                  25                  30

Thr Thr Ala Ala Arg Leu Thr Glu Asn Pro Asn Ile Ser Val Leu Val
        35                  40                  45

Ile Glu Ser Gly Ser Tyr Glu Ser Asp Arg Gly Pro Ile Ile Glu Asp
    50                  55                  60
```

```
Leu Asn Ala Tyr Gly Asp Ile Phe Gly Ser Ser Val Asp His Ala Tyr
 65                  70                  75                  80

Glu Thr Val Glu Leu Ala Thr Asn Asn Gln Thr Ala Leu Val Arg Ser
                 85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
            115                 120                 125

Glu Gly Trp Asn Trp Asp Asn Val Ala Ala Tyr Ser Leu Gln Ala Glu
            130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
            195                 200                 205

Pro His Gly Val Ser Met Phe Pro Asn Thr Leu His Glu Asp Gln Val
            210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
            275                 280                 285

Ala Gly Ser Ala Val Ser Pro Thr Ile Leu Glu Tyr Ser Gly Ile Gly
            290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
            355                 360                 365

Leu Asn Thr Lys Leu Glu Gln Trp Ala Glu Glu Ala Val Ala Arg Gly
            370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
            435                 440                 445

Ala Tyr Asp Pro Gln Tyr Phe Leu Asn Glu Leu Asp Leu Leu Gly Gln
            450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
```

```
                      485                 490                 495
Asp Ala Asp Leu Ser Ala Trp Thr Glu Tyr Ile Pro Tyr His Phe Arg
                500                 505                 510

Pro Asn Tyr His Gly Val Gly Thr Cys Ser Met Met Pro Lys Glu Met
            515                 520                 525

Gly Gly Val Val Asp Asn Ala Ala Arg Val Tyr Gly Val Gln Gly Leu
        530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580

<210> SEQ ID NO 2
<211> LENGTH: 583
<212> TYPE: PRT
<213> ORGANISM: Aspergillus niger

<400> SEQUENCE: 2

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Leu Thr Gly Leu
            20                  25                  30

Thr Thr Ala Ala Arg Leu Thr Glu Asn Pro Asn Ile Ser Val Leu Val
            35                  40                  45

Ile Glu Ser Gly Ser Tyr Glu Ser Asp Arg Gly Pro Ile Ile Glu Asp
        50                  55                  60

Leu Asn Ala Tyr Gly Asp Ile Phe Gly Ser Ser Val Asp His Ala Tyr
65              70                  75                  80

Glu Thr Val Glu Leu Ala Thr Asn Asn Gln Thr Ala Leu Ile Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
            115                 120                 125

Glu Gly Trp Asn Trp Asp Asn Val Ala Ala Tyr Ser Leu Gln Ala Glu
        130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205

Pro His Gly Val Ser Met Phe Pro Asn Thr Leu His Glu Asp Gln Val
    210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270
```

```
Lys Gly Asn Thr His Asn Val Tyr Ala Lys His Glu Val Leu Leu Ala
            275                 280                 285

Ala Gly Ser Ala Val Ser Pro Thr Ile Leu Glu Tyr Ser Gly Ile Gly
        290                 295                 300

Met Lys Ser Ile Leu Glu Pro Leu Gly Ile Asp Thr Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Ala Ala Trp Phe Ala
            340                 345                 350

Thr Phe Asn Glu Thr Phe Gly Asp Tyr Ser Lys Ala His Glu Leu
            355                 360                 365

Leu Asn Thr Lys Leu Glu Gln Trp Ala Glu Ala Val Ala Arg Gly
        370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
        435                 440                 445

Ala Tyr Asp Pro Gln Tyr Phe Leu Asn Glu Leu Asp Leu Leu Gly Gln
        450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
        515                 520                 525

Gly Gly Val Val Asp Asn Ala Ala Arg Val Tyr Gly Val Gln Gly Leu
530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580

<210> SEQ ID NO 3
<211> LENGTH: 583
<212> TYPE: PRT
<213> ORGANISM: Aspergillus niger

<400> SEQUENCE: 3

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Leu Val Gly Leu
            20                  25                  30

Thr Thr Ala Ala Arg Leu Thr Glu Asn Pro Asn Ile Ser Val Leu Val
        35                  40                  45

Ile Glu Ser Gly Ser Tyr Glu Ser Asp Arg Gly Pro Ile Ile Glu Asp
    50                  55                  60
```

-continued

```
Leu Asn Ala Tyr Gly Asp Ile Phe Gly Ser Ser Val Asp His Ala Tyr
 65                  70                  75                  80

Glu Thr Val Glu Leu Ala Thr Asn Asn Gln Thr Ala Leu Val Arg Ser
                 85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
            115                 120                 125

Glu Gly Trp Asn Trp Asp Asn Val Ala Ala Tyr Ser Leu Gln Ala Glu
            130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Val Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
            195                 200                 205

Pro His Gly Val Ser Met Phe Pro Asn Thr Leu His Glu Asp Gln Val
210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
            275                 280                 285

Ala Gly Ser Ala Val Ser Pro Thr Ile Leu Glu Tyr Ser Gly Ile Gly
            290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ser Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
            355                 360                 365

Leu Asn Thr Lys Leu Glu Gln Trp Ala Glu Glu Ala Val Ala Arg Gly
            370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Ile Leu Asp
                405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
            435                 440                 445

Ala Tyr Asp Pro Gln Tyr Phe Leu Asn Glu Leu Asp Leu Leu Gly Gln
            450                 455                 460

Ala Ala Ala Thr Gln Leu Ala Arg Asn Ile Ser Asn Ser Gly Ala Met
465                 470                 475                 480
```

```
Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
        515                 520                 525

Gly Gly Val Val Asp Asn Ala Ala Arg Val Tyr Gly Val Gln Gly Leu
    530                 535                 540

Arg Val Ile Asp Gly Ser Ile Pro Pro Thr Gln Met Ser Ser His Thr
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580

<210> SEQ ID NO 4
<211> LENGTH: 583
<212> TYPE: PRT
<213> ORGANISM: Aspergillus niger

<400> SEQUENCE: 4

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Gly Leu Val Gly Leu
            20                  25                  30

Thr Thr Ala Ala Arg Leu Thr Glu Asn Pro Asn Ile Ser Val Leu Val
        35                  40                  45

Ile Glu Ser Gly Ser Tyr Glu Ser Asp Arg Gly Pro Ile Ile Glu Asp
    50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Val Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
        115                 120                 125

Glu Gly Trp Asn Trp Asp Asn Val Ala Ala Tyr Ser Leu Gln Ala Glu
    130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ile Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205

Pro His Gly Val Ser Met Phe Pro Asn Thr Leu His Glu Asp Gln Val
    210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270
```

```
Lys Gly Asn Thr His Asn Val Tyr Ala Lys His Glu Val Leu Leu Ala
            275                 280                 285

Ala Gly Ser Ala Val Ser Pro Thr Ile Leu Glu Tyr Ser Gly Ile Gly
        290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ser Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
        355                 360                 365

Leu Asn Thr Lys Leu Glu Gln Trp Ala Glu Gly Val Ala Arg Gly
    370                 375                 380

Gly Phe His Asn Thr Thr Ala Leu Leu Ile Gln Tyr Glu Asn Tyr Arg
385                 390                 395                 400

Asp Trp Ile Val Asn His Val Ala Tyr Ser Glu Leu Leu Leu Asp
                405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
        435                 440                 445

Ala Tyr Asp Pro Gln Tyr Phe Leu Asn Glu Leu Asp Leu Leu Gly Gln
    450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
        515                 520                 525

Gly Gly Val Val Asp Asn Ala Ala Arg Val Tyr Gly Val Gln Gly Leu
    530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580

<210> SEQ ID NO 5
<211> LENGTH: 583
<212> TYPE: PRT
<213> ORGANISM: Aspergillus niger

<400> SEQUENCE: 5

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Gly Leu Val Gly Leu
                20                  25                  30

Thr Thr Ala Ala Arg Leu Thr Glu Asn Pro Asn Ile Ser Val Leu Val
            35                  40                  45

Ile Glu Ser Gly Ser Tyr Glu Ser Asp Arg Gly Pro Ile Ile Glu Asp
```

```
                50                  55                  60
Leu Asn Ala Tyr Gly Asp Ile Phe Gly Ser Ser Val Asp His Ala Tyr
 65                  70                  75                  80

Glu Thr Val Glu Leu Ala Thr Asn Asn Gln Thr Ala Leu Val Arg Ser
                 85                  90                  95

Gly Asn Gly Leu Gly Gly Ser Thr Leu Val Asn Gly Thr Trp Thr
                100                 105                 110

Arg Pro His Lys Ala Gln Val Asp Ser Trp Glu Thr Val Phe Gly Asn
                115                 120                 125

Glu Gly Trp Asn Trp Asp Asn Val Ala Ala Tyr Ser Leu Gln Ala Glu
            130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Val Gly Pro Arg
                165                 170                 175

Asp Thr Gly Asp Asp Tyr Ser Pro Ile Val Lys Ala Leu Met Ser Ala
                180                 185                 190

Val Glu Asp Arg Gly Val Pro Thr Lys Lys Asp Phe Gly Cys Gly Asp
                195                 200                 205

Pro His Gly Val Ser Met Phe Pro Asn Thr Leu His Glu Asp Gln Val
210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
                260                 265                 270

Lys Gly Asn Thr His Asn Val Tyr Ala Lys His Glu Val Leu Leu Ala
                275                 280                 285

Ala Gly Ser Ala Val Ser Pro Thr Ile Leu Glu Tyr Ser Gly Ile Gly
                290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Asn Thr Val Arg Ser
                325                 330                 335

Arg Ile Thr Ser Ala Gly Ala Gly Gln Gly Gln Ala Ala Trp Phe Ala
                340                 345                 350

Thr Phe Asn Glu Thr Phe Gly Asp Tyr Ser Glu Lys Ala His Glu Leu
                355                 360                 365

Leu Asn Thr Lys Leu Glu Gln Trp Ala Glu Glu Ala Val Ala Arg Gly
            370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
                420                 425                 430

Arg Gly Tyr Val His Ile Leu Asp Lys Asp Pro Tyr Leu His His Phe
                435                 440                 445

Ala Tyr Asp Pro Gln Tyr Phe Leu Asn Glu Leu Asp Leu Leu Gly Gln
                450                 455                 460

Ala Ala Ala Thr Gln Leu Ala Arg Asn Ile Ser Asn Ser Gly Ala Met
465                 470                 475                 480
```

```
Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
        515                 520                 525

Gly Gly Val Val Asp Asn Ala Ala Arg Val Tyr Gly Val Gln Gly Leu
    530                 535                 540

Arg Val Ile Asp Gly Ser Ile Pro Pro Thr Gln Met Ser Ser His Pro
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580

<210> SEQ ID NO 6
<211> LENGTH: 583
<212> TYPE: PRT
<213> ORGANISM: Aspergillus niger

<400> SEQUENCE: 6

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Leu Val Gly Leu
                20                  25                  30

Thr Thr Ala Ala Arg Leu Thr Glu Asn Pro Asn Ile Ser Val Leu Val
            35                  40                  45

Ile Glu Ser Gly Ser Tyr Glu Ser Asp Arg Gly Pro Ile Ile Glu Asp
        50                  55                  60

Leu Asn Ala Tyr Gly Asp Ile Phe Gly Ser Ser Val Asp His Ala Tyr
65                  70                  75                  80

Glu Thr Val Glu Leu Ala Thr Asn Asn Gln Thr Ala Leu Val Arg Ser
                85                  90                  95

Gly Asn Gly Leu Gly Gly Ser Thr Leu Val Asn Gly Gly Thr Trp Thr
            100                 105                 110

Arg Pro His Lys Ala Gln Val Asp Ser Trp Glu Thr Val Phe Gly Asn
        115                 120                 125

Glu Gly Trp Asn Trp Asp Asn Val Ala Ala Tyr Ser Leu Gln Ala Glu
    130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Val Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205

Pro His Gly Val Ser Met Phe Pro Asn Thr Leu His Glu Asp Gln Val
    210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
```

```
                260                 265                 270
Lys Gly Asn Thr His Asn Val Tyr Ala Lys His Glu Val Leu Leu Ala
            275                 280                 285

Ala Gly Ser Ala Val Ser Pro Thr Ile Leu Glu Tyr Ser Gly Ile Gly
        290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Asn Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
        355                 360                 365

Leu Asn Thr Lys Leu Glu Gln Trp Ala Glu Ala Val Ala Arg Gly
    370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Val Leu Asp
                405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
        435                 440                 445

Ala Tyr Asp Pro Gln Tyr Phe Leu Asn Glu Leu Asp Leu Leu Gly Gln
    450                 455                 460

Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
        515                 520                 525

Gly Gly Val Val Asp Asn Ala Ala Arg Val Tyr Gly Val Gln Gly Leu
    530                 535                 540

Arg Val Ile Asp Gly Ser Ile Pro Pro Thr Gln Met Ser Ser His Leu
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580

<210> SEQ ID NO 7
<211> LENGTH: 583
<212> TYPE: PRT
<213> ORGANISM: Aspergillus niger

<400> SEQUENCE: 7

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Leu Val Gly Leu
            20                  25                  30

Thr Thr Ala Ala Arg Leu Thr Glu Asn Pro Asn Ile Ser Val Leu Val
        35                  40                  45
```

Ile Glu Ser Gly Ser Tyr Glu Ser Asp Arg Gly Pro Ile Ile Glu Asp
 50                  55                  60

Leu Asn Ala Tyr Gly Asp Ile Phe Gly Ser Val Asp His Ala Tyr
 65                  70                  75                  80

Glu Thr Val Glu Leu Ala Thr Asn Asn Gln Thr Ala Leu Val Arg Ser
                 85                  90                  95

Gly Asn Gly Leu Gly Gly Ser Thr Leu Val Asn Gly Gly Thr Trp Thr
                100                 105                 110

Arg Pro His Lys Ala Gln Val Asp Ser Trp Glu Thr Val Phe Gly Asn
             115                 120                 125

Glu Gly Trp Asn Trp Asp Asn Val Ala Ala Tyr Ser Leu Gln Ala Glu
 130                 135                 140

Arg Ala Arg Ala Pro Asn Ala Lys Gln Ile Ala Ala Gly His Tyr Phe
 145                 150                 155                 160

Asn Ala Ser Cys His Gly Val Asn Gly Thr Val His Ala Gly Pro Arg
                 165                 170                 175

Asp Thr Gly Asp Asp Tyr Ser Pro Ile Val Lys Ala Leu Met Ser Ala
             180                 185                 190

Val Glu Asp Arg Gly Val Pro Thr Lys Lys Asp Phe Gly Cys Gly Asp
             195                 200                 205

Pro His Gly Val Ser Met Phe Pro Asn Thr Leu His Glu Asp Gln Val
 210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
             260                 265                 270

Lys Gly Asn Thr His Asn Val Tyr Ala Lys His Glu Val Leu Leu Ala
             275                 280                 285

Ala Gly Ser Ala Val Ser Pro Thr Ile Leu Glu Tyr Ser Gly Ile Gly
 290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ser Thr Val Arg Ser
                325                 330                 335

Arg Ile Thr Ser Ala Gly Ala Gly Gln Gly Gln Ala Ala Trp Phe Ala
             340                 345                 350

Thr Phe Asn Glu Thr Phe Gly Asp Tyr Ser Glu Lys Ala His Glu Leu
             355                 360                 365

Leu Asn Thr Lys Leu Glu Gln Trp Ala Glu Glu Ala Val Ala Arg Gly
 370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
             420                 425                 430

Arg Gly Tyr Val His Ile Leu Asp Lys Asp Pro Tyr Leu His His Phe
             435                 440                 445

Ala Tyr Asp Pro Gln Tyr Phe Leu Asn Glu Leu Asp Leu Leu Gly Gln
 450                 455                 460

Ala Ala Ala Thr Gln Leu Ala Arg Asn Ile Ser Asn Ser Gly Ala Met

```
                465                 470                 475                 480
        Gln Thr Tyr Phe Ala Gly Glu Thr Ile Pro Gly Asp Asn Leu Ala Tyr
                        485                 490                 495

Asp Ala Asp Leu Ser Ala Trp Thr Glu Tyr Ile Pro Tyr His Phe Arg
                    500                 505                 510

Pro Asn Tyr His Gly Val Gly Thr Cys Ser Met Met Pro Lys Glu Met
                    515                 520                 525

Gly Gly Val Val Asp Asn Ala Ala Arg Val Tyr Gly Val Gln Gly Leu
                    530                 535                 540

Arg Val Ile Asp Gly Ser Ile Pro Thr Gln Met Ser Ser His Pro
        545                 550                 555                 560

Met Thr Val Phe Tyr Ala Met Ala Leu Lys Ile Ser Asp Ala Ile Leu
                        565                 570                 575

Glu Asp Tyr Ala Ser Met Gln
                        580

<210> SEQ ID NO 8
<211> LENGTH: 583
<212> TYPE: PRT
<213> ORGANISM: Aspergillus niger

<400> SEQUENCE: 8

Ser Asn Gly Ile Glu Ala Ser Leu Leu Thr Asp Pro Lys Asp Val Ser
        1               5                   10                  15

Gly Arg Thr Val Asp Tyr Ile Ile Ala Gly Gly Leu Val Gly Leu
                    20                  25                  30

Thr Thr Ala Ala Arg Leu Thr Glu Asn Pro Asn Ile Ser Val Leu Val
                        35                  40                  45

Ile Glu Ser Gly Phe Tyr Glu Ser Asp Arg Gly Pro Ile Ile Glu Asp
            50                  55                  60

Leu Asn Ala Tyr Gly Asp Ile Phe Gly Ser Ser Val Asp His Ala Tyr
        65                  70                  75                  80

Glu Thr Val Glu Leu Ala Thr Asn Asn Gln Thr Ala Leu Val Arg Ser
                        85                  90                  95

Gly Asn Gly Leu Gly Gly Ser Thr Leu Val Asn Gly Gly Thr Trp Thr
                    100                 105                 110

Arg Pro His Lys Ala Gln Val Asp Ser Trp Glu Thr Val Phe Gly Asn
                    115                 120                 125

Glu Gly Trp Asn Trp Asp Asn Val Ala Ala Tyr Ser Leu Gln Ala Glu
        130                 135                 140

Arg Ala Arg Ala Pro Asn Ala Lys Gln Ile Ala Ala Gly His Tyr Phe
        145                 150                 155                 160

Asn Ala Ser Cys His Gly Val Asn Gly Thr Val His Ala Gly Pro Arg
                        165                 170                 175

Asp Thr Gly Asp Asp Tyr Ser Pro Ile Val Lys Ala Leu Met Ser Ala
                    180                 185                 190

Val Glu Asp Arg Gly Val Pro Thr Lys Lys Asp Phe Gly Cys Gly Asp
                    195                 200                 205

Pro His Gly Val Ser Met Phe Pro Asn Thr Leu His Glu Asp Gln Val
                    210                 215                 220

Arg Ser Asp Ala Ala Arg Glu Trp Leu Leu Pro Asn Tyr Gln Arg Pro
        225                 230                 235                 240

Asn Leu Gln Val Leu Thr Gly Gln Tyr Val Gly Lys Val Leu Leu Ser
                        245                 250                 255
```

```
Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
        275                 280                 285

Ala Gly Ser Ala Val Ser Pro Thr Ile Leu Glu Tyr Ser Gly Ile Gly
    290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ser Thr Val Arg Ser
                325                 330                 335

Arg Ile Thr Ser Ala Gly Ala Gln Gly Gln Ala Ala Trp Phe Ala
            340                 345                 350

Thr Phe Asn Glu Thr Phe Gly Asp Tyr Ser Glu Lys Ala His Glu Leu
            355                 360                 365

Leu Asn Thr Lys Leu Glu Gln Trp Ala Glu Ala Val Ala Arg Gly
            370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
            435                 440                 445

Ala Tyr Asp Pro Gln Tyr Phe Leu Asn Glu Leu Asp Leu Leu Gly Gln
    450                 455                 460

Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
            515                 520                 525

Gly Gly Val Val Asp Asn Ala Ala Arg Val Tyr Gly Val Gln Gly Leu
530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
            565                 570                 575

Glu Asp Tyr Ala Ser Met Gln
            580

<210> SEQ ID NO 9
<211> LENGTH: 583
<212> TYPE: PRT
<213> ORGANISM: Aspergillus niger

<400> SEQUENCE: 9

Ser Asn Gly Ile Glu Ala Ser Leu Leu Thr Asp Pro Lys Asp Val Ser
1               5                   10                  15

Gly Arg Thr Val Asp Tyr Ile Ile Ala Gly Gly Gly Leu Val Gly Leu
            20                  25                  30

Thr Thr Ala Ala Arg Leu Thr Glu Asn Pro Asn Ile Ser Val Leu Val
        35                  40                  45
```

-continued

```
Ile Glu Ser Gly Ser Tyr Glu Ser Asp Arg Gly Pro Ile Ile Glu Asp
 50              55                  60

Leu Asn Ala Tyr Gly Asp Ile Phe Gly Ser Ser Val Asp His Ala Tyr
 65              70                  75                  80

Glu Thr Val Glu Leu Ala Thr Asn Asn Gln Thr Ala Leu Val Arg Ser
                 85                  90                  95

Gly Asn Gly Leu Gly Gly Ser Thr Leu Val Asn Gly Gly Thr Trp Thr
                100                 105                 110

Arg Pro His Lys Ala Gln Val Asp Ser Trp Glu Thr Val Phe Gly Asn
            115                 120                 125

Glu Gly Trp Asn Trp Asp Asn Val Leu Ala Tyr Ser Leu Gln Ala Glu
        130                 135                 140

Arg Ala Arg Ala Pro Asn Ala Lys Gln Ile Ala Ala Gly His Tyr Phe
145                 150                 155                 160

Asn Ala Ser Cys His Gly Val Asn Gly Thr Val His Ala Gly Pro Arg
                165                 170                 175

Asp Thr Gly Asp Asp Tyr Ser Pro Ile Val Lys Ala Leu Met Ser Ala
            180                 185                 190

Val Glu Asp Arg Gly Val Pro Thr Lys Lys Asp Phe Gly Cys Gly Asp
        195                 200                 205

Pro His Gly Val Ser Met Phe Pro Asn Thr Leu His Glu Asp Gln Val
210                 215                 220

Arg Ser Asp Ala Ala Arg Glu Trp Leu Leu Pro Asn Tyr Gln Arg Pro
225                 230                 235                 240

Asn Leu Gln Val Leu Thr Gly Gln Tyr Val Gly Lys Val Leu Leu Ser
                245                 250                 255

Gln Asn Gly Thr Thr Pro Arg Ala Val Gly Val Glu Phe Gly Thr His
            260                 265                 270

Lys Gly Asn Thr His Asn Val Tyr Ala Lys His Glu Val Leu Leu Ala
        275                 280                 285

Ala Gly Ser Ala Val Ser Pro Thr Ile Leu Glu Tyr Ser Gly Ile Gly
290                 295                 300

Met Lys Ser Ile Leu Glu Pro Leu Gly Ile Asp Thr Val Val Asp Leu
305                 310                 315                 320

Pro Val Gly Leu Asn Leu Gln Asp Gln Thr Thr Ala Thr Val Arg Ser
                325                 330                 335

Arg Ile Thr Ser Ala Gly Ala Gly Gln Gly Gln Ala Ala Trp Phe Ala
            340                 345                 350

Thr Phe Asn Glu Thr Phe Gly Asp Tyr Ser Glu Lys Ala His Glu Leu
        355                 360                 365

Leu Asn Thr Lys Leu Glu Gln Trp Ala Glu Ala Val Ala Arg Gly
370                 375                 380

Gly Phe His Asn Thr Thr Ala Leu Leu Ile Gln Tyr Glu Asn Tyr Arg
385                 390                 395                 400

Asp Trp Ile Val Asn His Asn Val Ala Tyr Ser Glu Leu Phe Leu Asp
                405                 410                 415

Thr Ala Gly Val Ala Ser Phe Asp Val Trp Asp Leu Leu Pro Phe Thr
            420                 425                 430

Arg Gly Tyr Val His Ile Leu Asp Lys Asp Pro Tyr Leu His His Phe
        435                 440                 445

Ala Tyr Asp Pro Gln Tyr Phe Leu Asn Glu Leu Asp Leu Leu Gly Gln
450                 455                 460
```

```
Ala Ala Ala Thr Gln Leu Ala Arg Asn Ile Ser Asn Ser Gly Ala Met
465                 470                 475                 480

Gln Thr Tyr Phe Ala Gly Glu Thr Ile Pro Gly Asp Asn Leu Ala Tyr
                485                 490                 495

Asp Ala Asp Leu Ser Ala Trp Thr Glu Tyr Ile Pro Tyr His Phe Arg
            500                 505                 510

Pro Asn Tyr His Gly Val Gly Thr Cys Ser Met Met Pro Lys Glu Met
        515                 520                 525

Gly Gly Val Val Asp Asn Ala Arg Val Tyr Gly Val Gln Gly Leu
    530                 535                 540

Arg Val Ile Asp Gly Ser Ile Pro Pro Thr Gln Met Ser Ser His Val
545                 550                 555                 560

Met Thr Val Phe Tyr Ala Met Ala Leu Lys Ile Ser Asp Ala Ile Leu
                565                 570                 575

Glu Asp Tyr Ala Ser Met Gln
            580

<210> SEQ ID NO 10
<211> LENGTH: 1749
<212> TYPE: DNA
<213> ORGANISM: Aspergillus niger

<400> SEQUENCE: 10
agcaatggca ttgaagccag cctcctgact gatcccaagg atgtctccgg ccgcacggtc      60
gactacatca tcgctggtgg aggtctggtt ggactcacca ccgctgctcg tctgacggag     120
aaccccaaca tcagtgtgct cgtcatcgaa agtggctcct acgagtcgga cagaggtcct     180
atcattgagg acctgaacgc ctacggcgac atctttggca gcagtgtaga ccacgcctac     240
gagaccgtgg agctcgctac caacaatcaa accgcgctgg tccgctccgg aaatggtctc     300
ggtggctcta ctctagtgaa tggtggcacc tggactcgcc cccacaaggc acaggttgac     360
tcttgggaga ctgtctttgg aaatgagggc tggaactggg acaatgtggc cgcctactcc     420
ctccaggctg agcgtgctcg cgcaccaaat gccaaacaga tcgctgctgg ccactacttc     480
aacgcatcct gccatggtgt taatggtact gtccatgccg accccgcgca caccggcgat     540
gactattctc ccatcgtcaa ggctctcatg agcgctgtcg aagaccgggg cgttcccacc     600
aagaaagact tcgatgcggt gaccccccat ggtgtgtcca tgttccccaa caccttgcac     660
gaagaccaag tgcgctccga tgccgctcgc gaatggctac ttcccaacta ccaacgtccc     720
aacctgcaag tcctgaccgg acagtatgtt ggtaaggtgc tccttagcca gaacggcacc     780
accccctcgt ccgttggcgt ggaattcggc acccacaagg gcaacaccca caacgtttac     840
gctaagcacg aggtcctcct ggccgcgggc tccgctgtct ctcccacaat cctcgaatat     900
tccggtatcg gaatgaagtc catcctggag cccttggta tcgacaccgt cgttgacctg     960
cccgtcggct tgaacctgca ggaccagacc accgctaccg tccgctcccg catcacctct    1020
gctggtgcag gacagggaca ggccgcttgg ttcgccacct tcaacgagac ctttggtgac    1080
tattccgaaa aggcacacga gctgctcaac accaagctgg agcagtgggc cgaagaggcc    1140
gtcgcccgtg gcggattcca caacaccacc gccttgctca tccagtacga gaactaccgc    1200
gactggattg tcaaccacaa cgtcgcgtac tcggaactct tcctcgacac tgccggagta    1260
gccagcttcg atgtgtggga ccttctgccc ttcacccgag gatacgttca catcctcgac    1320
aaggaccccc accttcacca cttcgcctac gaccctcagt acttcctcaa cgagctggac    1380
ctgctcggtc aggctgccgc tactcaactg gcccgcaaca tctccaactc cggtgccatg    1440
```

```
cagacctact tcgctgggga gactatcccc ggtgataacc tcgcgtatga tgccgatttg    1500
agcgcctgga ctgagtacat cccgtaccac ttccgtccta actaccatgg cgtgggtact    1560
tgctccatga tgccgaagga gatgggcggt gttgttgata tgctgcccg tgtgtatggt     1620 gtgcagggac tgcgtgtcat tgatggttct attcctccta cgcaaatgtc gtcccatgtc    1680
atgacggtgt tctatgccat ggcgctaaaa atttcggatg ctatcttgga agattatgct    1740
tccatgcag                                                            1749

<210> SEQ ID NO 11
<211> LENGTH: 1749
<212> TYPE: DNA
<213> ORGANISM: Aspergillus niger

<400> SEQUENCE: 11
agcaatggca ttgaagccag cctcctgact gatcccaagg atgtctccgg ccgcacggtc     60
gactacatca tcgctggtgg aggtctggtt ggactcacca ccgctgctcg tctgacggag    120
aaccccaaca tcagtgtgct cgtcatcgaa agtggctcct acgagtcgga cagaggtcct    180
atcattgagg acctgaacgc ctacggcgac atctttggca gcagtgtaga ccacgcctac    240
gagaccgtgg agctcgctac caacaatcaa accgcgctgg tccgctccgg aaatggtctc    300
ggtggctcta ctctagtgaa tggtggcacc tggactcgcc cccacaaggc acaggttgac    360
tcttgggaga ctgtctttgg aaatgagggc tggaactggg acaatgtggc cgcctactcc    420
ctccaggctg agcgtgctcg cgcaccaaat gccaaacaga tcgctgctgg ccactacttc    480
aacgcatcct gccatggtgt taatggtact gtccatgttg accccgcga caccggcgat    540 gactattctc ccatcgtcaa ggctctcatg agcgctgtcg aagaccgggg cgttcccacc    600
aagaaagact tcggatgcgg tgaccccat ggtgtgtcca tgttcccaa caccttgcac     660 gaagaccaag tgcgctccga tgccgctcgc gaatggctac ttcccaacta ccaacgtccc    720
aacctgcaag tcctgaccgg acagtatgtt ggtaaggtgc tccttagcca gaacggcacc    780 accctcgtg ccgttggcgt ggaattcggc acccacaagg caacaccca caacgtttac      840 gctaagcacg aggtcctcct ggccgcgggc tccgctgtct ctcccacaat cctcgaatat    900
tccggtatcg gaatgaagtc catcctggag ccccttggta tcgacaccgt cgttgacctg    960
cccgtcggct tgaacctgca ggaccagacc accagtaccg tccgctcccg catcacctct    1020
gctggtgcag gacagggaca ggccgcttgg ttcgccacct tcaacgagac ctttggtgac    1080
tattccgaaa aggcacacga gctgctcaac accaagctgg agcagtgggc cgaagaggcc    1140
gtcgcccgtg gcggattcca caacaccacc gccttgctca tccagtacga gaactaccgc    1200
gactggattg tcaaccacaa cgtcgcgtac tcggaactaa ttctcgacac tgccggagta    1260
gccagcttcg atgtgtggga ccttctgccc ttcacccgag atacgttca tcctcgac       1320 aaggacccct accttcacca cttcgcctac gaccctcagt acttcctcaa cgagctggac    1380
ctgctcggtc aggctgccgc tactcaactg gcccgcaaca tctccaactc cggtgccatg    1440
cagacctact tcgctgggga gactatcccc ggtgataacc tcgcgtatga tgccgatttg    1500
agcgcctgga ctgagtacat cccgtaccac ttccgtccta actaccatgg cgtgggtact    1560
tgctccatga tgccgaagga gatgggcggt gttgttgata tgctgcccg tgtgtatggt     1620 gtgcagggac tgcgtgtcat tgatggttct attcctccta cgcaaatgtc gtcccatacg    1680
atgacggtgt tctatgccat ggcgctaaaa atttcggatg ctatcttgga agattatgct    1740
```

```
tccatgcag                                                              1749

<210> SEQ ID NO 12
<211> LENGTH: 1749
<212> TYPE: DNA
<213> ORGANISM: Aspergillus niger

<400> SEQUENCE: 12
agcaatggca ttgaagccag cctcctgact gatcccaagg atgtctccgg ccgcacggtc     60
gactacatca tcgctggtgg aggtctggtt ggactcacca ccgctgctcg tctgacggag    120
aaccccaaca tcagtgtgct cgtcatcgaa agtggctcct acgagtcgga cagaggtcct    180
atcattgagg acctgaacgc ctacggcgac atctttggca gcagtgtaga ccacgcctac    240
gagaccgtgg agctcgctac caacaatcaa accgcgctgg tccgctccgg aaatggtctc    300
ggtggctcta ctctagtgaa tggtggcacc tggactcgcc cccacaaggc acaggttgac    360
tcttgggaga ctgtctttgg aaatgagggc tggaactggg acaatgtggc cgcctactcc    420
ctccaggctg agcgtgctcg cgcaccaaat gccaaacaga tcgctgctgg ccactacttc    480
aacgcatcct gccatggtgt taatggtact gtccatattg accccgcga caccggcgat    540 gactattctc ccatcgtcaa ggctctcatg agcgctgtcg aagaccgggg cgttcccacc    600
aagaaagact tcggatgcgg tgaccccat ggtgtgtcca tgttccccaa caccttgcac    660
gaagaccaag tgcgctccga tgccgctcgc gaatggctac ttcccaacta ccaacgtccc    720
aacctgcaag tcctgaccgg acagtatgtt ggtaaggtgc tccttagcca gaacggcacc    780 accccctcgtg ccgttggcgt ggaattcggc acccacaagg gcaacaccca caacgtttac    840
gctaagcacg aggtcctcct ggccgcgggc tccgctgtct ctcccacaat cctcgaatat    900
tccggtatcg gaatgaagtc catcctggag ccccttggta tcgacaccgt cgttgacctg    960
cccgtcggct tgaacctgca ggaccagacc accagtaccg tccgctcccg catcacctct    1020
gctggtgcag acagggaca ggccgcttgg ttcgccacct tcaacgagac ctttggtgac    1080
tattccgaaa aggcacacga gctgctcaac accaagctgg agcagtgggc cgaagaggcc    1140
gtcgcccgtg gcggattcca caacaccacc gccttgctca tccagtacga gaactaccgc    1200
gactggattg tcaaccacaa cgtcgcgtac tcggaactcc ttctcgacac tgccggagta    1260
gccagcttcg atgtgtggga ccttctgccc ttcacccgag atacgttca catcctcgac    1320 aaggacccct accttcacca cttcgcctac gaccctcagt acttcctcaa cgagctggac    1380
ctgctcggtc aggctgccgc tactcaactg gcccgcaaca tctccaactc cggtgccatg    1440
cagacctact tcgctgggga gactatcccc ggtgataacc tcgcgtatga tgccgatttg    1500
agcgcctgga ctgagtacat cccgtaccac ttcgtcccta actaccatgg cgtgggtact    1560
tgctccatga tgccgaagga gatgggcggt gttgttgata atgctgcccg tgtgtatggt    1620
gtgcagggac tgcgtgtcat tgatggttct attcctccta cgcaaatgtc gtcccatgtc    1680
atgacggtgt tctatgccat ggcgctaaaa atttcggatg ctatcttgga agattatgct    1740
tccatgcag                                                              1749

<210> SEQ ID NO 13
<211> LENGTH: 1749
<212> TYPE: DNA
<213> ORGANISM: Aspergillus niger

<400> SEQUENCE: 13
agcaatggca ttgaagccag cctcctgact gatcccaagg atgtctccgg ccgcacggtc     60
```

```
gactacatca tcgctggtgg aggtctggtt ggactcacca ccgctgctcg tctgacggag      120
aaccccaaca tcagtgtgct cgtcatcgaa agtggctcct acgagtcgga cagaggtcct      180
atcattgagg acctgaacgc ctacggcgac atctttggca gcagtgtaga ccacgcctac      240
gagaccgtgg agctcgctac caacaatcaa accgcgctgg tccgctccgg aaatggtctc      300
ggtggctcta ctctagtgaa tggtggcacc tggactcgcc cccacaaggc acaggttgac      360
tcttgggaga ctgtctttgg aaatgagggc tggaactggg acaatgtggc cgcctactcc      420
ctccaggctg agcgtgctcg cgcaccaaat gccaaacaga tcgctgctgg ccactacttc      480
aacgcatcct gccatggtgt taatggtact gtccatgttg accccgcga caccggcgat      540 gactattctc ccatcgtcaa ggctctcatg agcgctgtcg aagaccgggg cgttcccacc      600
aagaaagact tcggatgcgg tgaccccat ggtgtgtcca tgttccccaa cacccttgcac      660 gaagaccaag tgcgctccga tgccgctcgc gaatggctac ttcccaacta ccaacgtccc      720
aacctgcaag tcctgaccgg acagtatgtt ggtaaggtgc tccttagcca gaacggcacc      780
acccctcgtg ccgttggcgt ggaattcggc acccacaagg gcaacaccca caacgtttac      840
gctaagcacg aggtcctcct ggccgcgggc tccgctgtct ctcccacaat cctcgaatat      900
tccggtatcg gaatgaagtc catcctggag ccccttggta tcgacaccgt cgttgacctg      960
cccgtcggct tgaacctgca ggaccagacc accaataccg tccgctcccg catcacctct     1020
gctggtgcag acagggaca ggccgcttgg ttcgccacct caacgagac ctttggtgac     1080 tattccgaaa aggcacacga gctgctcaac accaagctgg agcagtgggc cgaagaggcc     1140
gtcgcccgtg gcggattcca caacaccacc gccttgctca tccagtacga gaactaccgc     1200
gactggattg tcaaccacaa cgtcgcgtac tcggaactct ttctcgacac tgccggagta     1260
gccagcttcg atgtgtggga ccttctgccc ttcacccgag gatacgttca catcctcgac     1320
aaggacccct accttcacca cttcgcctac gaccctcagt acttcctcaa cgagctggac     1380
ctgctcggtc aggctgccgc tactcaactg gcccgcaaca tctccaactc cggtgccatg     1440
cagacctact cgctggggga gactatcccc ggtgataacc tcgcgtatga tgccgatttg     1500
agcgcctgga ctgagtacat cccgtaccac ttccgtccta actaccatgg cgtgggtact     1560
tgctccatga tgccgaagga gatgggcggt gttgttgata tgctgcccg tgtgtatggt     1620 gtgcagggac tgcgtgtcat tgatggttct attcctccta cgcaaatgtc gtcccatccg     1680
atgacggtgt tctatgccat ggcgctaaaa atttcggatg ctatcttgga agattatgct     1740
tccatgcag                                                             1749
```

<210> SEQ ID NO 14
<211> LENGTH: 1749
<212> TYPE: DNA
<213> ORGANISM: Aspergillus niger

<400> SEQUENCE: 14

```
agcaatggca ttgaagccag cctcctgact gatcccaagg atgtctccgg ccgcacggtc       60
gactacatca tcgctggtgg aggtctggtt ggactcacca ccgctgctcg tctgacggag      120
aaccccaaca tcagtgtgct cgtcatcgaa agtggctcct acgagtcgga cagaggtcct      180
atcattgagg acctgaacgc ctacggcgac atctttggca gcagtgtaga ccacgcctac      240
gagaccgtgg agctcgctac caacaatcaa accgcgctgg tccgctccgg aaatggtctc      300
ggtggctcta ctctagtgaa tggtggcacc tggactcgcc cccacaaggc acaggttgac      360
```

```
tcttgggaga ctgtctttgg aaatgagggc tggaactggg acaatgtggc cgcctactcc    420
ctccaggctg agcgtgctcg cgcaccaaat gccaaacaga tcgctgctgg ccactacttc    480
aacgcatcct gccatggtgt taatggtact gtccatgttg accccgcga caccggcgat    540 gactattctc ccatcgtcaa ggctctcatg agcgctgtcg aagaccgggg cgttcccacc    600
aagaaagact tcggatgcgg tgaccccat ggtgtgtcca tgttcccaa caccttgcac    660 gaagaccaag tgcgctccga tgccgctcgc gaatggctac ttcccaacta ccaacgtccc    720
aacctgcaag tcctgaccgg acagtatgtt ggtaaggtgc tccttagcca gaacggcacc    780 accccctcgtg ccgttggcgt ggaattcggc acccacaagg gcaacaccca caacgtttac    840
gctaagcacg aggtcctcct ggccgcgggc tccgctgtct ctcccacaat cctcgaatat    900
tccggtatcg gaatgaagtc catcctggag ccccttggta tcgacaccgt cgttgacctg    960
cccgtcggct tgaacctgca ggaccagacc accaataccg tccgctcccg catcacctct   1020
gctggtgcag gacagggaca ggccgcttgg ttcgccacct caacgagac ctttggtgac   1080 tattccgaaa aggcacacga gctgctcaac accaagctgg agcagtgggc cgaagaggcc   1140
gtcgcccgtg gcggattcca caacaccacc gccttgctca tccagtacga gaactaccgc   1200
gactggattg tcaaccacaa cgtcgcgtac tcggaactcg ttctcgacac tgccggagta   1260
gccagcttcg atgtgtggga ccttctgccc ttcacccgag atacgttca tcctcgac     1320 aaggaccccct accttcacca cttcgcctac gaccctcagt acttcctcaa cgagctggac   1380
ctgctcggtc aggctgccgc tactcaactg gcccgcaaca tctccaactc cggtgccatg   1440
cagacctact tcgctgggga gactatcccc ggtgataacc tcgcgtatga tgccgatttg   1500
agcgcctgga ctgagtacat cccgtaccac ttccgtccta actaccatgg cgtgggtact   1560
tgctccatga tgccgaagga gatgggcggt gttgttgata tgctgccccg tgtgtatggt   1620
gtgcagggac tgcgtgtcat tgatggttct attcctccta cgcaaatgtc gtcccatctg   1680
atgacggtgt tctatgccat ggcgctaaaa atttcggatg ctatcttgga agattatgct   1740
tccatgcag                                                           1749
```

<210> SEQ ID NO 15
<211> LENGTH: 1749
<212> TYPE: DNA
<213> ORGANISM: Aspergillus niger

<400> SEQUENCE: 15

```
agcaatggca ttgaagccag cctcctgact gatcccaagg atgtctccgg ccgcacggtc     60
gactacatca tcgctggtgg aggtctggtt ggactcacca ccgctgctcg tctgacggag    120
aaccccaaca tcagtgtgct cgtcatcgaa agtggctcct acgagtcgga cagaggtcct    180
atcattgagg acctgaacgc ctacggcgac atctttggca gcagtgtaga ccacgcctac    240
gagaccgtgg agctcgctac caacaatcaa accgcgctgg tccgctccgg aaatggtctc    300
ggtggctcta ctctagtgaa tggtggcacc tggactcgcc ccacaaggc acaggttgac    360 tcttgggaga ctgtctttgg aaatgagggc tggaactggg acaatgtggc cgcctactcc    420
ctccaggctg agcgtgctcg cgcaccaaat gccaaacaga tcgctgctgg ccactacttc    480
aacgcatcct gccatggtgt taatggtact gtccatgccg accccgcga caccggcgat    540 gactattctc ccatcgtcaa ggctctcatg agcgctgtcg aagaccgggg cgttcccacc    600
aagaaagact tcggatgcgg tgaccccat ggtgtgtcca tgttcccaa caccttgcac    660 gaagaccaag tgcgctccga tgccgctcgc gaatggctac ttcccaacta ccaacgtccc    720
```

```
aacctgcaag tcctgaccgg acagtatgtt ggtaaggtgc tccttagcca gaacggcacc      780
acccctcgtg ccgttggcgt ggaattcggc acccacaagg caacaccca caacgtttac      840
gctaagcacg aggtcctcct ggccgcgggc tccgctgtct ctcccacaat cctcgaatat     900
tccggtatcg gaatgaagtc catcctggag ccccttggta tcgacaccgt cgttgacctg     960
cccgtcggct tgaacctgca ggaccagacc accagtaccg tccgctcccg catcacctct   1020
gctggtgcag gacagggaca ggccgcttgg ttcgccacct caacgagac ctttggtgac    1080
tattccgaaa aggcacacga gctgctcaac accaagctgg agcagtgggc cgaagaggcc   1140
gtcgcccgtg gcggattcca caacaccacc gccttgctca tccagtacga gaactaccgc   1200
gactggattg tcaaccacaa cgtcgcgtac tcggaactct tcctcgacac tgccggagta   1260
gccagcttcg atgtgtggga ccttctgccc ttcacccgag gatacgttca catcctcgac   1320
aaggacccct accttcacca cttcgcctac gaccctcagt acttcctcaa cgagctggac   1380
ctgctcggtc aggctgccgc tactcaactg gcccgcaaca tctccaactc cggtgccatg   1440
cagacctact tcgctgggga gactatcccc ggtgataacc tcgcgtatga tgccgatttg   1500
agcgcctgga ctgagtacat cccgtaccac ttccgtccta actaccatgg cgtgggtact   1560
tgctccatga tgccgaagga gatgggcggt gttgttgata atgctgcccg tgtgtatggt   1620
gtgcagggac tgcgtgtcat tgatggttct attcctccta cgcaaatgtc gtcccatccg   1680
atgacggtgt tctatgccat ggcgctaaaa atttcggatg ctatcttgga agattatgct   1740
tccatgcag                                                              1749

<210> SEQ ID NO 16
<211> LENGTH: 1749
<212> TYPE: DNA
<213> ORGANISM: Aspergillus niger

<400> SEQUENCE: 16
agcaatggca ttgaagccag cctcctgact gatcccaagg atgtctccgg ccgcacggtc    60
gactacatca tcgctggtgg aggtctggtt ggactcacca ccgctgctcg tctgacggag   120
aaccccaaca tcagtgtgct cgtcatcgaa agtggcttct acgagtcgga cagaggtcct   180
atcattgagg acctgaacgc ctacggcgac atctttggca gcagtgtaga ccacgcctac   240
gagaccgtgg agctcgctac caacaatcaa accgcgctgg tccgctccgg aaatggtctc   300
ggtggctcta ctctagtgaa tggtggcacc tggactcgcc cccacaaggc acaggttgac   360
tcttgggaga ctgtctttgg aaatgagggc tggaactggg acaatgtggc cgcctactcc   420
ctccaggctg agcgtgctcg cgcaccaaat gccaaacaga tcgctgctgg ccactacttc   480
aacgcatcct gccatggtgt taatggtact gtccatgccg accccgcgca caccggcgat   540
gactattctc ccatcgtcaa ggctctcatg agcgctgtcg aagaccgggg cgttcccacc   600
aagaaagact tcgatgcgcg tgaccccat ggtgtgtcca tgttcccaa cacccttgcac   660
gaagaccaag tgcgctccga tgccgctcgc gaatggctac ttcccaacta ccaacgtccc   720
aacctgcaag tcctgaccgg acagtatgtt ggtaaggtgc tccttagcca gaacggcacc   780
acccctcgtg ccgttggcgt ggaattcggc acccacaagg caacaccca caacgtttac     840
gctaagcacg aggtcctcct ggccgcgggc tccgctgtct ctcccacaat cctcgaatat   900
tccggtatcg gaatgaagtc catcctggag ccccttggta tcgacaccgt cgttgacctg    960
cccgtcggct tgaacctgca ggaccagacc accagtaccg tccgctcccg catcacctct  1020
```

```
gctggtgcag gacagggaca ggccgcttgg ttcgccacct tcaacgagac ctttggtgac    1080
tattccgaaa aggcacacga gctgctcaac accaagctgg agcagtgggc cgaagaggcc    1140
gtcgcccgtg gcggattcca caacaccacc gccttgctca tccagtacga gaactaccgc    1200
gactggattg tcaaccacaa cgtcgcgtac tcggaactct tcctcgacac tgccggagta    1260
gccagcttcg atgtgtggga ccttctgccc ttcacccgag gatacgttca catcctcgac    1320
aaggacccct accttcacca cttcgcctac gaccctcagt acttcctcaa cgagctggac    1380
ctgctcggtc aggctgccgc tactcaactg gcccgcaaca tctccaactc cggtgccatg    1440
cagacctact cgctgggga gactatcccc ggtgataacc tcgcgtatga tgccgatttg    1500
agcgcctgga ctgagtacat cccgtaccac ttccgtccta actaccatgg cgtgggtact    1560
tgctccatga tgccgaagga gatgggcggt gttgttgata tgctgcccg tgtgtatggt    1620 gtgcagggac tgcgtgtcat tgatggttct attcctccta cgcaaatgtc gtcccatgtc    1680
atgacggtgt tctatgccat ggcgctaaaa atttcggatg ctatcttgga agattatgct    1740
tccatgcag                                                            1749

<210> SEQ ID NO 17
<211> LENGTH: 1749
<212> TYPE: DNA
<213> ORGANISM: Aspergillus niger

<400> SEQUENCE: 17
agcaatggca ttgaagccag cctcctgact gatcccaagg atgtctccgg ccgcacggtc      60
gactacatca tcgctggtgg aggtctggtt ggactcacca ccgctgctcg tctgacggag     120
aaccccaaca tcagtgtgct cgtcatcgaa agtggctcct acgagtcgga cagaggtcct     180
atcattgagg acctgaacgc ctacggcgac atctttggca gcagtgtaga ccacgcctac     240
gagaccgtgg agctcgctac caacaatcaa accgcgctgg tccgctccgg aaatggtctc     300
ggtggctcta ctctagtgaa tggtggcacc tggactcgcc ccacaaggc acaggttgac      360 tcttgggaga ctgtctttgg aaatgagggc tggaactggg acaatgtgtt ggcctactcc     420
ctccaggctg agcgtgctcg cgcaccaaat gccaaacaga tcgctgctgg ccactacttc     480
aacgcatcct gccatggtgt taatggtact gtccatgccg accccgcga caccggcgat     540 gactattctc ccatcgtcaa ggctctcatg agcgctgtcg aagaccgggg cgttcccacc     600
aagaaagact cggatgcgg tgaccccat ggtgtgtcca tgttccccaa caccttgcac      660
gaagaccaag tgcgctccga tgccgctcgc gaatggctac ttcccaacta ccaacgtccc     720
aacctgcaag tcctgaccgg acagtatgtt ggtaaggtgc tccttagcca gaacggcacc     780 accctcgtg ccgttggcgt ggaattcggc acccacaagg gcaacaccca caacgtttac      840
gctaagcacg aggtcctcct ggccgcgggc tccgctgtct ctcccacaat cctcgaatat     900
tccggtatcg gaatgaagtc catcctggag ccccttggta tcgacaccgt cgttgacctg     960
cccgtcggct tgaacctgca ggaccagacc accgctaccg tccgctcccg catcacctct    1020
gctggtgcag gacagggaca ggccgcttgg ttcgccacct tcaacgagac ctttggtgac    1080
tattccgaaa aggcacacga gctgctcaac accaagctgg agcagtgggc cgaagaggcc    1140
gtcgcccgtg gcggattcca caacaccacc gccttgctca tccagtacga gaactaccgc    1200
gactggattg tcaaccacaa cgtcgcgtac tcggaactct tcctcgacac tgccggagta    1260
gccagcttcg atgtgtggga ccttctgccc ttcacccgag gatacgttca catcctcgac    1320
aaggacccct accttcacca cttcgcctac gaccctcagt acttcctcaa cgagctggac    1380
```

```
ctgctcggtc aggctgccgc tactcaactg gcccgcaaca tctccaactc cggtgccatg    1440
cagacctact tcgctgggga gactatcccc ggtgataacc tcgcgtatga tgccgatttg    1500
agcgcctgga ctgagtacat cccgtaccac ttccgtccta actaccatgg cgtgggtact    1560
tgctccatga tgccgaagga gatgggcggt gttgttgata atgctgcccg tgtgtatggt    1620
gtgcagggac tgcgtgtcat tgatggttct attcctccta cgcaaatgtc gtcccatgtc    1680
atgacggtgt tctatgccat ggcgctaaaa atttcggatg ctatcttgga agattatgct    1740
tccatgcag                                                            1749
```

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18

```
ggcgtgaatg taagcgtgac ata                                              23
```

<210> SEQ ID NO 19
<211> LENGTH: 40
<212> TYPE: DNA
<213> ORGANISM: Artificial Sequence
<220> FEATURE:
<223> OTHER INFORMATION: Primer

<400> SEQUENCE: 19

```
cacactaccg cactccgtcg ccggatcgga ctactagcag                            40
```

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20

```
ccggatcgga ctactagcag                                                  20
```

<210> SEQ ID NO 21
<211> LENGTH: 43
<212> TYPE: DNA
<213> ORGANISM: Artificial Sequence
<220> FEATURE:
<223> OTHER INFORMATION: Primer

<400> SEQUENCE: 21

```
gtgtgatggc gtgaggcagc ggcgtgaatg taagcgtgac ata                        43
```

<210> SEQ ID NO 22
<211> LENGTH: 59
<212> TYPE: DNA
<213> ORGANISM: Artificial Sequence
<220> FEATURE:
<223> OTHER INFORMATION: Primer

<400> SEQUENCE: 22

```
gtggtctccc tcgctgcggc cctgccacac tacatcagga gcaatggcat tgaagccag       59
```

<210> SEQ ID NO 23
<211> LENGTH: 60
<212> TYPE: DNA

```
<213> ORGANISM: Artificial Sequence
<220> FEATURE:
<223> OTHER INFORMATION: Primer

<400> SEQUENCE: 23
attacatgat gcggccctct agatgcatgc tcgagcggcc gccagtgtga tggatatctg    60

<210> SEQ ID NO 24
<211> LENGTH: 29
<212> TYPE: DNA
<213> ORGANISM: Artificial Sequence
<220> FEATURE:
<223> OTHER INFORMATION: Primer

<400> SEQUENCE: 24
ggtactgtcc atrytggacc ccgcgacac                                     29

<210> SEQ ID NO 25
<211> LENGTH: 25
<212> TYPE: DNA
<213> ORGANISM: Artificial Sequence
<220> FEATURE:
<223> OTHER INFORMATION: Primer

<400> SEQUENCE: 25
ggtggtctgg tcctgcaggt tcaag                                         25

<210> SEQ ID NO 26
<211> LENGTH: 28
<212> TYPE: DNA
<213> ORGANISM: Artificial Sequence
<220> FEATURE:
<223> OTHER INFORMATION: Primer

<400> SEQUENCE: 26
gaccagacca ccartaccgt ccgctccc                                      28

<210> SEQ ID NO 27
<211> LENGTH: 25
<212> TYPE: DNA
<213> ORGANISM: Artificial Sequence
<220> FEATURE:
<223> OTHER INFORMATION: Primer

<400> SEQUENCE: 27
gagttccgag tacgcgacgt tgtgg                                         25

<210> SEQ ID NO 28
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(13)
<223> OTHER INFORMATION: n is a, c, g, or t

<400> SEQUENCE: 28
tactcggaac tcndtctcga cactgcc                                       27

<210> SEQ ID NO 29
<211> LENGTH: 24
<212> TYPE: DNA
<213> ORGANISM: Artificial Sequence
<220> FEATURE:
<223> OTHER INFORMATION: Primer
```

```
<400> SEQUENCE: 29
atgggacgac atttgcgtag gagg                                              24

<210> SEQ ID NO 30
<211> LENGTH: 29
<212> TYPE: DNA
<213> ORGANISM: Artificial Sequence
<220> FEATURE:
<223> OTHER INFORMATION: Primer

<400> SEQUENCE: 30
atgtcgtccc atvykatgac ggtgttcta                                         29

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
atggacagta ccattaacac catg                                              24

<210> SEQ ID NO 32
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 32
ggtactgtcc atnnkggacc ccgcgacac                                         29

<210> SEQ ID NO 33
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t

<400> SEQUENCE: 33
gtgtcgcggg gtccmnnatg gacagtacc                                         29

<210> SEQ ID NO 34
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 34
gaccagacca ccnnkaccgt ccgctccc                                          28

<210> SEQ ID NO 35
```

```
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (15)..(16)
<223> OTHER INFORMATION: n is a, c, g, or t

<400> SEQUENCE: 35
gggagcggac ggtmnnggtg gtctggtc                                           28

<210> SEQ ID NO 36
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 36
tactcggaac tcnnkctcga cactgcc                                            27

<210> SEQ ID NO 37
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (14)..(15)
<223> OTHER INFORMATION: n is a, c, g, or t

<400> SEQUENCE: 37
ggcagtgtcg agmnngagtt ccgagta                                            27

<210> SEQ ID NO 38
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(14)
<223> OTHER INFORMATION: n is a, c, g, or t

<400> SEQUENCE: 38
atgtcgtccc atnnkatgac ggtgttcta                                          29

<210> SEQ ID NO 39
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t

<400> SEQUENCE: 39
tagaacaccg tcatmnnatg ggacgacat                                          29
```

```
<210> SEQ ID NO 40
<211> LENGTH: 12
<212> TYPE: PRT
<213> ORGANISM: Artificial Sequence
<220> FEATURE:
<223> OTHER INFORMATION: Miscellaneous sequence

<400> SEQUENCE: 40

Arg Asn Asp Cys Gly His Ile Leu Phe Ser Thr Val
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Miscellaneous sequence

<400> SEQUENCE: 41

Ala Ile Leu Met Pro Thr Val
1               5
```